US009480644B2

(12) United States Patent
Crystal et al.

(10) Patent No.: US 9,480,644 B2
(45) Date of Patent: *Nov. 1, 2016

(54) NASAL DRUG PRODUCTS AND METHODS OF THEIR USE

(71) Applicant: Lightlake Therapeutics, Inc., New York, NY (US)

(72) Inventors: Roger Crystal, Santa Monica, CA (US); Michael Brenner Weiss, New York, NY (US)

(73) Assignee: Opiant Pharmaceuticals, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/942,344

(22) Filed: Nov. 16, 2015

(65) Prior Publication Data

US 2016/0166503 A1 Jun. 16, 2016

Related U.S. Application Data

(63) Continuation-in-part of application No. 14/659,472, filed on Mar. 16, 2015, now Pat. No. 9,211,253.

(60) Provisional application No. 61/953,379, filed on Mar. 14, 2014.

(51) Int. Cl.
| A61M 31/00 | (2006.01) |
| A61M 5/00  | (2006.01) |
| A61F 13/00 | (2006.01) |
| A61K 31/56 | (2006.01) |
| A61K 9/00  | (2006.01) |
| A61K 31/485| (2006.01) |
| A61M 11/00 | (2006.01) |
| A61K 47/02 | (2006.01) |
| A61K 47/18 | (2006.01) |
| A61K 9/08  | (2006.01) |
| A61M 15/08 | (2006.01) |

(52) U.S. Cl.
CPC ............... *A61K 9/0043* (2013.01); *A61K 9/08* (2013.01); *A61K 31/485* (2013.01); *A61K 47/02* (2013.01); *A61K 47/183* (2013.01); *A61K 47/186* (2013.01); *A61M 11/006* (2014.02); *A61M 15/08* (2013.01); *A61M 31/00* (2013.01)

(58) Field of Classification Search
None
See application file for complete search history.

(56) References Cited

U.S. PATENT DOCUMENTS

| 4,181,726 A | 1/1980 | Bernstein |
| 4,464,378 A | 8/1984 | Hussain |
| 5,866,154 A | 2/1999 | Bahal et al. |
| 9,192,570 B2 * | 11/2015 | Wyse .................. A61K 9/0043 |
| 9,211,253 B2 | 12/2015 | Crystal et al. |
| 2003/0077300 A1 | 4/2003 | Wermeling |
| 2006/0120967 A1 | 6/2006 | Namburi et al. |
| 2009/0017102 A1 | 1/2009 | Stinchcomb et al. |
| 2010/0113495 A1 | 5/2010 | Wermeling et al. |
| 2010/0168147 A1 | 7/2010 | Chapleo et al. |
| 2010/0331354 A1 | 12/2010 | Wermeling |
| 2011/0046172 A1 | 2/2011 | Chapleo et al. |
| 2012/0270895 A1 | 10/2012 | Wermeling |
| 2013/0023825 A1 | 1/2013 | Edwards et al. |
| 2015/0174061 A1 | 6/2015 | Wyse et al. |
| 2016/0008277 A1 | 1/2016 | Crystal et al. |

FOREIGN PATENT DOCUMENTS

| CN | 1575795 | 2/2005 |
| EP | 1681057 B1 | 8/2008 |
| WO | WO 8203768 A1 | 11/1982 |
| WO | WO 9830211 A1 | 7/1998 |
| WO | WO 0062757 A1 | 10/2000 |
| WO | WO 0074652 A1 | 12/2000 |
| WO | WO 0158447 A1 | 8/2001 |
| WO | WO 0182931 A1 | 11/2001 |
| WO | WO 0211778 A1 | 2/2002 |
| WO | WO 03084520 A2 | 10/2003 |
| WO | WO 2004054511 A2 | 7/2004 |
| WO | WO 2005020906 A2 | 3/2005 |
| WO | WO 2006089973 A2 | 8/2006 |
| WO | WO 2007083073 A1 | 7/2007 |
| WO | WO 2009040595 A1 | 2/2009 |
| WO | WO 2012026963 A2 | 3/2012 |
| WO | WO 2012156317 A2 | 11/2012 |
| WO | WO 2013128447 A1 | 9/2013 |
| WO | WO 2014016653 A1 | 1/2014 |
| WO | WO 2015095644 A1 | 6/2015 |
| WO | WO 2015136373 A1 | 9/2015 |
| WO | WO 2015136373 A3 | 9/2015 |
| WO | WO 2016007729 A1 | 1/2016 |

OTHER PUBLICATIONS

U.S. Appl. No. 14/950,707, filed Nov. 24, 2015, Lightlake Therapeutics Inc.
Walley, A Y et al, "Opioid overdose rates and implementation of overdose education and nasal naloxone distribution in Massachusetts: interrupted time series analysis," BMJ 346:f174, (Published Jan. 31, 2013).
Walley A Y et al., "Opioid overdose prevention with intranasal naloxone among people who take methadone," J Subst Abuse Treat 44:2, 241-47 (Epub Sep. 12, 2012).
Weber J M et al., "Can nebulized naloxone be used safely and effectively by emergency medical services for suspected opioid overdose?"Prehosp Emerg Care 16:2, 289-92 (Epub Dec. 22, 2011).
Merlin M A et al., "Intranasal naloxone delivery is an alternative to intravenous naloxone for opioid overdoses," Am J Emerg Med 28:3, 296-303 (Epub Jan. 28, 2010).
Kerr D et al., "Randomized controlled trial comparing the effectiveness and safety of intranasal and intramuscular naloxone for the treatment of suspected heroin overdose," Addiction 104:12, 2067-74 (Epub Nov. 9, 2009).

(Continued)

*Primary Examiner* — Jeffrey T Palenik
(74) *Attorney, Agent, or Firm* — Dennis A. Bennett; Cynthia Hathaway

(57) ABSTRACT

Drug products adapted for nasal delivery, comprising a pre-primed device filled with a pharmaceutical composition comprising an opioid receptor antagonist, are provided. Methods of treating opioid overdose or its symptoms with the inventive drug products are also provided.

69 Claims, 7 Drawing Sheets

(56) References Cited

OTHER PUBLICATIONS

Robertson T M, "Intranasal naloxone is a viable alternative to intravenous naloxone for prehospital narcotic overdose," Prehosp Emerg Care 13:4, 512-15 (Published Oct. 2009).

Doe-Simkins M et al., "Saved by the nose: bystander-administered intranasal naloxone hydrochloride for opioid overdose," Am J Public Health 99:5, 788-91 (published May 2009).

Heard C et al., "Intranasal flumazenil and naloxone to reverse over-sedation in a child undergoing dental restorations," Paediatr Anaesth 19:8 795-99 (published Aug. 2009).

Dowling J et al., "Population pharmacokinetics of intravenous, intramuscular, and intranasal naloxone in human volunteers," Ther Drug Monit 30:4 490-96 (published Aug. 2008).

Ashton H et al., "Best evidence topic report. Intranasal naloxone in suspected opioid overdose," Emerg Med J 23:3, 221-23 (published Mar. 2006).

Barton E D et al., "Efficacy of intranasal naloxone as a needleless alternative for treatment of opioid overdose in the prehospital setting," J Emerg Med 29:3, 265-71 (published Oct. 2005).

Kelly A M et al., "Randomised trial of intranasal versus intramuscular naloxone in prehospital treatment for suspected opioid overdose," Med J Aust 182:1 24-27 (published Jan. 3, 2005).

Kelly A M et al., "Intranasal naloxone for life threatening opioid toxicity," Emerg Med J 19:4, 375 (published Jul. 2002).

Barton E D et al., "Intranasal administration of naloxone by paramedics," Prehosp Emerg Care 6:1, 54-58 (published Jan. 2002).

Loimer N et al., "Nasal administration of naloxone is as effective as the intravenous route in opiate addicts," Int J Addict 29:6, 819-27 (published Apr. 1994).

Loimer N et al., "Nasal administration of naloxone for detection of opiate dependence," J Psychiatr Res 26:1, 39-43 (published Jan. 1992).

Bailey A M et al., "Naloxone for opioid overdose prevention: pharmacists' role in community-based practice settings," Ann. Pharmacother 48:5, 601-06 (published May 2014).

Wermeling D P et al., "A response to the opioid overdose epidemic: naloxone nasal spray," Drug Delivery Transl. Res. 3:1, 63-74 (published Feb. 1, 2013).

Wermeling D P et al., "Opioid harm reduction strategies: focus on expanded access to intranasal naloxone," Pharmacotherapy 30:7, 627-31, 2010.

Aptar UnitDose and BiDose product information sheet, available at www.aptar.com/docs/pharma-prescription/uds-bds-datasheet.pdf, publication date unknown, last accessed Mar. 26, 2015.

Crystal r. et al., Nasal drug products and methods of their use, Lightlake Therapeutics, Inc., U.S. Appl. No. 14/659,472, Notice of Allowance,Oct. 9, 2015.

Crystal r. et al., Nasal drug products and methods of their use, Lightlake Therapeutics, Inc., U.S. Appl. No. 14/659,472, Notice of Allowance,Nov. 9, 2015.

U.S. Appl. No. 15/183,441, filed Jun. 14, 2016, Keegan F. et al.

Keegan F. et al., Pharmacokinetic Propertoes and Human Use Characteristics of an FDA Approved Intranasal Naloxone Product for the Treatment of Opioid Overdose, J Clin Pharmacol, 2016, pp. 1-11, First published online: Jun. 10, 2016.

International Search Report and Written Opinion for WO2016/007729, Dec. 4, 2015, 16 pages.

* cited by examiner

3A

3B

4A

4B

Two Sprays 20 mg/mL

6A

One Spray 40 mg/mL

6B

NASAL DRUG PRODUCTS AND METHODS OF THEIR USE

This application is a continuation-in-part of U.S. application Ser. No. 14/659,472, filed Mar. 16, 2015, which claims the benefit of U.S. Provisional Application No. 61/953,379, filed Mar. 14, 2014, the disclosure of which is hereby incorporated by reference as if written herein in its entirety.

Provided are drug products adapted for nasal delivery comprising a pre-primed device and a pharmaceutical composition comprising an opioid receptor antagonist, pharmaceutical compositions comprising an opioid receptor antagonist, and methods of use thereof.

Opioid receptors are G protein-coupled receptors (GPCRs) that are activated both by endogenous opioid peptides and by clinically important alkaloid analgesic drugs such as morphine. There are three principal types of opioid receptors: the δ-opioid receptor, the κ-opioid receptor, and the μ-opioid receptor. Opioids depress respiration, which is controlled principally through medullary respiratory centers with peripheral input from chemoreceptors and other sources. Opioids produce inhibition at the chemoreceptors via μ-opioid receptors and in the medulla via μ- and δ-opioid receptors. While there are a number of neurotransmitters mediating the control of respiration, glutamate and γ-aminobutyric acid (GABA) are the major excitatory and inhibitory neurotransmitters, respectively. This explains the potential for interaction of opioids with benzodiazepines and alcohol: both benzodiazepines and alcohol facilitate the inhibitory effect of GABA at the GABAA receptor, while alcohol also decreases the excitatory effect of glutamate at NMDA receptors. Oxycodone and other opioid painkillers, as well as heroin and methadone are all implicated in fatal overdose. Heroin has three metabolites with opioid activity. Variation in the formation of these metabolites due to genetic factors and the use of other drugs could explain differential sensitivity to overdose. Metabolites of methadone contribute little to its action. However, variation in rate of metabolism due to genetic factors and other drugs used can modify methadone concentration and hence overdose risk. The degree of tolerance also determines risk. Tolerance to respiratory depression is less than complete, and may be slower than tolerance to euphoric and other effects. One consequence of this may be a relatively high risk of overdose among experienced opioid users. While agonist administration modifies receptor function, changes (usually in the opposite direction) also result from use of antagonists, for example, supersensitivity to opioids following a period of administration of antagonists such as naltrexone.

In the United States, mortality rates closely correlate with opioid sales. In 2008, approximately 36,450 people died from drug overdoses. At least 14,800 of these deaths involved prescription opioid analgesics. Moreover, according to the Substance Abuse and Mental Health Services Administration, the number/rate of Americans 12 years of age and older who currently abuse pain relievers has increased by 20 percent between 2002 and 2009. In New York City, between 1990 and 2006, the fatality rate from prescription opioids increased seven-fold, from 0.39 per 100,000 persons to 2.7. Drugs classed as prescription opioids in this study include both typical analgesics, such as OxyContin® (oxycodone HCl controlled-release) and methadone (used in the treatment of dependence on other opioids such as heroin and also prescribed for pain), but the increase in the rate of drug overdose over the 16 years of the study was driven entirely by overdoses of typical analgesics. Over the same time period, methadone overdoses remained stable, and overdoses from heroin declined. Whites were more likely than blacks and Latinos to overdose on these analgesics, and deaths mostly occurred in neighborhoods with lower rates of poverty, suggesting differential access to doctors who can write painkiller prescriptions may be a driving force behind the racial disparity. (Cerdá et al. "*Prescription opioid mortality trends in New York City, 1990-2006: Examining the emergence of an epidemic,*" Drug and Alcohol Dependence Volume 132, Issues 1-2, 1 Sep. 2013, 53-62.)

Naloxone is an opioid receptor antagonist that is approved for use by injection for the reversal of opioid overdose and for adjunct use in the treatment of septic shock. It is currently being used mainly in emergency departments and in ambulances by trained medical professionals. There have been efforts to expand its use by providing the drug to some patients with take-home opioid prescriptions and those who inject illicit drugs, potentially facilitating earlier administration of the drug. The UN Commission on Narcotics Drugs "encourages all Member States to include effective elements for the prevention and treatment of drug overdose, in particular opioid overdose, in national drug policies, where appropriate, and to share best practices and information on the prevention and treatment of drug overdose, in particular opioid overdose, including the use of opioid receptor antagonists such as naloxone."

U.S. Pat. No. 4,464,378 describes a method for eliciting an analgesic or narcotic antagonist response in a warm-blooded animal, which comprises administering intranasally (IN) to said animal to elicit a narcotic antagonist response, a narcotic antagonist effective amount of naloxone. WO 82/03768 discloses a composition that contains 1 mg of naloxone hydrochloride per 0.1 ml of solution adapted for nasal administration used in the treatment of narcotic induced respiratory depression (overdose) at a dosage approximately the same as that employed for intravenous (IV), intramuscular (IM) or subcutaneous (SQ) administration. WO 00/62757 teaches pharmaceutical compositions for IN or oral (PO) administration which comprise an opioid antagonist, such as naloxone for application by spray in the reversal of opioid depression for treatment of patients suffering from opioid over-dosage, wherein the spray applicator is capable of delivering single or multiple doses and suitable dosage units are in the range of 0.2 to 5 mg.

The use of nasal naloxone is not without controversy. For instance, Loimer et al. (International Journal of Addictions, 29(6), 819-827, 1994) reported that the nasal administration of naloxone is as effective as the intravenous route in opiate addicts, however, Dowling et al. (Ther Drug Monit, Vol 30, No 4, August 2008) reported that naloxone administered intranasally displays a relative bioavailability of 4% only and concluded that the IN absorption is rapid but does not maintain measurable concentrations for more than an hour.

One early study of 196 consecutive patients with suspected opioid overdose conducted in an urban out-of-hospital setting, had shown the mean interval from emergency medical services (EMS) arrival to a respiratory rate of ≥10 breaths/min was 9.3±4.2 min with administration of naloxone 0.4 mg IV, versus 9.6±4.58 min with administration of naloxone 0.8 mg SQ. The authors concluded that the slower rate of absorption via the SQ route was offset by the delay in establishing an IV line. (Wanger et al., *Intravenous vs subcutaneous naloxone for out-of-hospital management of presumed opioid overdose*. Acad Emerg Med. 1998 April; 5(4):293-9).

The Denver Health Paramedic system subsequently investigated the efficacy and safety of atomized intranasal naloxone for the treatment of suspected opiate overdose (Barton, et al., *Efficacy of intranasal naloxone as a needleless alternative for treatment of opioid overdose in the prehospital setting*. J Emerg Med, 2005. 29(3): p. 265-71). All adult patients encountered in the prehospital setting as suspected opiate overdose, found down, or with altered mental status who met the criteria for naloxone administration were included in the study. IN naloxone (2 mg) was administered immediately upon patient contact and before IV insertion and administration of IV naloxone (2 mg). Patients were then treated by EMS protocol. The main outcome measures were: time of IN naloxone administration, time of IV naloxone administration, time of appropriate patient response as reported by paramedics. Ninety-five patients received IN naloxone and were included in the study. A total of 52 patients responded to naloxone by either IN or IV, with 43 (83%) responding to IN naloxone alone. Seven patients (16%) in this group required further doses of IV naloxone. The median times from arrival at patient side to awakening and from administration of the IN naloxone to patient awakening were 8.0 minutes and 3.0 minutes respectively.

The Drug Overdose Prevention and Education (DOPE) Project was the first naloxone prescription program (NPP) established in partnership with a county health department (San Francisco Department of Public Health), and is one of the longest running NPPs in the USA. From September 2003 to December 2009, 1,942 individuals were trained and prescribed naloxone through the DOPE Project, of whom 24% returned to receive a naloxone refill, and 11% reported using naloxone during an overdose event. Of 399 overdose events where naloxone was used, participants reported that 89% were reversed. In addition, 83% of participants who reported overdose reversal attributed the reversal to their administration of naloxone, and fewer than 1% reported serious adverse effects. Findings from the DOPE Project add to a growing body of research that suggests that intravenous drug users (IDUs) at high risk of witnessing overdose events are willing to be trained on overdose response strategies and use take-home naloxone during overdose events to prevent deaths (Enteen, et al., *Overdose prevention and naloxone prescription for opioid users in San Francisco*. J Urban Health. 2010 December; 87(6):931-41).

Another reported study reviewed EMS and hospital records before and after implementation of a protocol for administration of intranasal naloxone by the Central California EMS Agency in order to compare the prehospital time intervals from patient contact and medication administration to clinical response for IN versus intravenous IV naloxone in patients with suspected narcotic overdose. The protocol for the treatment of opioid overdose with intranasal naloxone was as follows: "Intranasal (IN)—Administer 2 mg intranasally (1 mg per nostril) using mucosal atomizer device (MAD™) if suspected narcotic intoxication and respiratory depression (rate 8 or less). This dose may be repeated in 5 minutes if respiratory depression persists. Respirations should be supported with a bag valve mask until respiratory rate is greater than 8. Intramuscular (IM)—Administer 1 mg if unable to administer intranasally (see special considerations). May repeat once in 5 minutes. Intravenous (IV)—Administer 1 mg slow IV push if no response to intranasal or IM administration after 10 minutes. Pediatric dose—0.1 mg/kg intranasally, if less than 10 kg and less than 1 year old". Patients with suspected narcotic overdose treated in the prehospital setting over 17 months, between March 2003 and July 2004 were included. Paramedics documented dose, route of administration, and positive response times using an electronic record. Clinical response was defined as an increase in respiratory rate (breaths/min) or Glasgow Coma Scale score of at least 6. Main outcome variables included time from medication to clinical response and time from patient contact to clinical response. Secondary variables included numbers of doses administered and rescue doses given by an alternate route. Between-group comparisons were accomplished using t-tests and chi-square tests as appropriate. One hundred fifty-four patients met the inclusion criteria, including 104 treated with IV and 50 treated with IN naloxone. Clinical response was noted in 33 (66%) and 58 (56%) of the IN and IV groups, respectively (p=0.3). The mean time between naloxone administration and clinical response was longer for the IN group (12.9 vs. 8.1 min, p=0.02). However, the mean times from patient contact to clinical response were not significantly different between the IN and IV groups (20.3 vs. 20.7 min, p=0.9). More patients in the IN group received two doses of naloxone (34% vs. 18%, p=0.05), and three patients in the IN group received a subsequent dose of IV or IM naloxone. (Robertson et al., *Intranasal naloxone is a viable alternative to intravenous naloxone for prehospital narcotic overdose*. Prehosp Emerg Care. 2009 October-December; 13(4):512-5).

In August 2006, the Boston Public Health Commission passed a public health regulation that authorized an opioid overdose prevention program that included intranasal naloxone education and distribution of the spray to potential bystanders. Participants were instructed by trained staff to deliver 1 mL (1 mg) to each nostril of the overdose victim. After 15 months, the program had provided training and intranasal naloxone to 385 participants who reported 74 successful overdose reversals (Doe-Simkins et al. *Overdose prevention education with distribution of intranasal naloxone is a feasible public health intervention to address opioid overdose*. Am J Public Health. 2009; 99:788-791).

Overdose education and nasal naloxone distribution (OEND) programs are community-based interventions that educate people at risk for overdose and potential bystanders on how to prevent, recognize and respond to an overdose. They also equip these individuals with a naloxone rescue kit. To evaluate the impact of OEND programs on rates of opioid related death from overdose and acute care utilization in Massachusetts, an interrupted time series analysis of opioid related overdose death and acute care utilization rates from 2002 to 2009 was performed comparing community-year strata with high and low rates of OEND implementation to those with no implementation. The setting was nineteen Massachusetts communities (geographically distinct cities and towns) with at least five fatal opioid overdoses in each of the years 2004 to 2006. OEND was implemented among opioid users at risk for overdose, social service agency staff, family, and friends of opioid users. OEND programs equipped people at risk for overdose and bystanders with nasal naloxone rescue kits and trained them how to prevent, recognize, and respond to an overdose by engaging emergency medical services, providing rescue breathing, and delivering naloxone. Among these communities, OEND programs trained 2,912 potential bystanders who reported 327 rescues. Both community-year strata with 1-100 enrollments per 100,000 population (adjusted rate ratio 0.73, 95% confidence interval 0.57 to 0.91) and community-year strata with greater than 100 enrollments per 100,000 population (0.54, 0.39 to 0.76) had significantly reduced adjusted rate ratios compared with communities with no implementation.

Differences in rates of acute care hospital utilization were not significant. Opioid overdose death rates were reduced in communities where OEND was implemented. This study provides observational evidence that by training potential bystanders to prevent, recognize, and respond to opioid overdoses, OEND is an effective intervention (Walley et al., *Opioid overdose rates and implementation of overdose education and nasal naloxone distribution in Massachusetts: interrupted time series analysis*. BMJ 2013; 346: f174).

Naloxone prescription programs are also offered by community-based organizations in Los Angeles and Philadelphia. Programs in both cities target IDUs. Studies which recruited 150 IDUs across both sites for in-depth qualitative interviews compared two groups of IDUs, those who had received naloxone prescriptions and those who had never received naloxone prescriptions. In both L.A. and Philadelphia, IDUs reported successfully administering naloxone to reverse recently witnessed overdoses. Reversals often occurred in public places by both housed and homeless IDUs. Despite these successes, IDUs frequently did not have naloxone with them when they witnessed an overdose. Two typical reasons reported were naloxone was confiscated by police, and IDUs did not feel comfortable carrying naloxone in the event of being stopped by police. Similarly, some untrained IDUs reported discomfort with the idea of carrying naloxone on them as their reason for not gaining a prescription.

A randomized trial comparing 2 mg naloxone delivered intranasally with a mucosal atomizer to 2 mg intramuscular naloxone was reported by Kelly et al., in 2005 (Med J Aust. 2005 Jan. 3; 182(1):24-7). The study involved 155 patients (71 IM and 84 IN) requiring treatment for suspected opiate overdose and attended by paramedics of the Metropolitan Ambulance Service (MAS) and Rural Ambulance Victoria in Victoria, Australia. The IM group had more rapid response than the IN group, and were more likely to have more than 10 spontaneous respirations per minute within 8 minutes (82% v. 63%; P=0.0173). There was no statistically significant difference between the IM and IN groups for needing rescue naloxone (13% [TM group] v. 26% [IN group]; P=0.0558). The authors concluded that IN naloxone is effective in treating opiate-induced respiratory depression, but is not as effective as IM naloxone.

Kerr et al. (Addiction. 2009 December; 104(12):2067-74) disclosed treatment of heroin overdose by intranasal administration of naloxone constituted in a vial as a preparation of 2 mg in 1 mL. Participants received 1 mg (0.5 ml) in each nostril. The rate of response within 10 minutes was 60/83 (72.3%) for 2 mg IN naloxone versus 69/89 (77.5%) for 2 mg IM naloxone. The mean response times were 8.0 minutes and 7.9 minutes for IN and IV naloxone respectively. Supplementary naloxone was administered to fewer patients who received IM naloxone (4.5%) than IN (18.1%).

WO2012156317 describes a study in which naloxone, 8 mg and 16 mg, was administered as 400 µL IN (200 µL per nostril). The administration was performed as follows: The pump of the nasal spray was primed by removing the cap and pressing downward. This is repeated at least 6 times or until a fine spray appears; priming is done just prior to dosing. The subject is in a standing or upright position and should gently blow the nose to clear the nostrils. The subject should tilt the head forward slightly and gently close one nostril by pressing the outside of the nose with a finger on the nostril to be closed. The device is inserted into the open nostril and it is sprayed 2 times into the nostril. The subject should gently breath inward through the nostril, the device is removed, and the steps are repeated for the other nostril. The mean $T_{max}$ values were reported to be 0.34 h (20.4 min) and 0.39 h (23.4 min) for the 8 and 16 mg doses respectively.

Wermeling (Drug Deliv Transl Res. 2013 Feb. 1; 3(1): 63-74) teaches that the initial adult dose of naloxone in known or suspected narcotic overdose is 0.4 to 2 mg, which may be repeated to a total dose of 10 mg and that the current formulations of naloxone are approved for intravenous (IV), intramuscular (IM) and subcutaneous (SC) administration, with IV being the recommended route. Wermeling also predicts that a 2 mg nasal solution dose of naloxone will likely have a $C_{max}$ of 3-5 ng/mL and a $t_{max}$ of approximately 20 minutes.

Since the onset of action of naloxone used in opioid overdose cases should be as fast as possible, naloxone is thus far mainly administered intravenously or intramuscularly by emergency health care personnel. Due to a high first pass metabolism, oral dosage forms comprising naloxone display a low bioavailability and thus seem to be not suitable for such purposes. The administration of naloxone via injection into the blood stream or into the muscle requires first of all trained medical personnel (for intravenous injection) or a trained carer (for intramuscular injection). Secondly, depending on the constitution of the addict and the period of intravenous drug abuse, it can be particularly difficult to find access into a vein of the addict's body for administering naloxone intravenously. Clearly, there is a risk of exposure to blood borne pathogens for the medical personnel or the trained carer since a large population of drug addicts suffers from blood borne pathogen induced diseases such as HIV, hepatitis B and C, and the like since accidental needlestick is a serious safety concern. 385,000 needle-stick injuries have been estimated to have occurred in the year 2000 in the US alone (Wilburn, *Needlestick and sharps injury prevention*, Online J Issues Nurs 2004, Sep. 30; 9(3):5).

Naloxone has a relatively short half-life of compared to some longer-acting opioid formulations and so after a typical therapeutic dose of naloxone is administered to an opioid overdose patient there is often the need to re-administer naloxone, in some cases even several times, and it is important to seek immediate medical attention.

Furthermore, it has been suggested that in view of the growing opioid overdose crisis in the US, naloxone should be made available over-the-counter (OTC), which would require a device, such as a nasal spray device, that untrained consumers are able to use safely. A nasal spray device that was pre-filled with a naloxone formulation would also be less likely to be confiscated by police than the system developed by some EMS programs that combines an FDA-approved naloxone injection product with a marketed, medical device called the Mucosal Atomization Device.

Thus, there remains a need for durable, easy-to-use, needleless devices with storage-stable formulations, that can enable untrained individuals to quickly deliver a therapeutically effective dose of a rapid-acting opioid antagonist to an opioid overdose patient. The therapeutically effective dose should be sufficient to obviate the need for the untrained individual to administer either a second dose of opioid antagonist or an alternative medical intervention to the patient, and to stabilize the patient until professional medical care becomes available. The devices described herein meet this and other needs.

Provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride.

Also provided are methods of treating opioid overdose or a symptom thereof, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride.

DETAILED DESCRIPTION OF THE INVENTION

Figure 1:
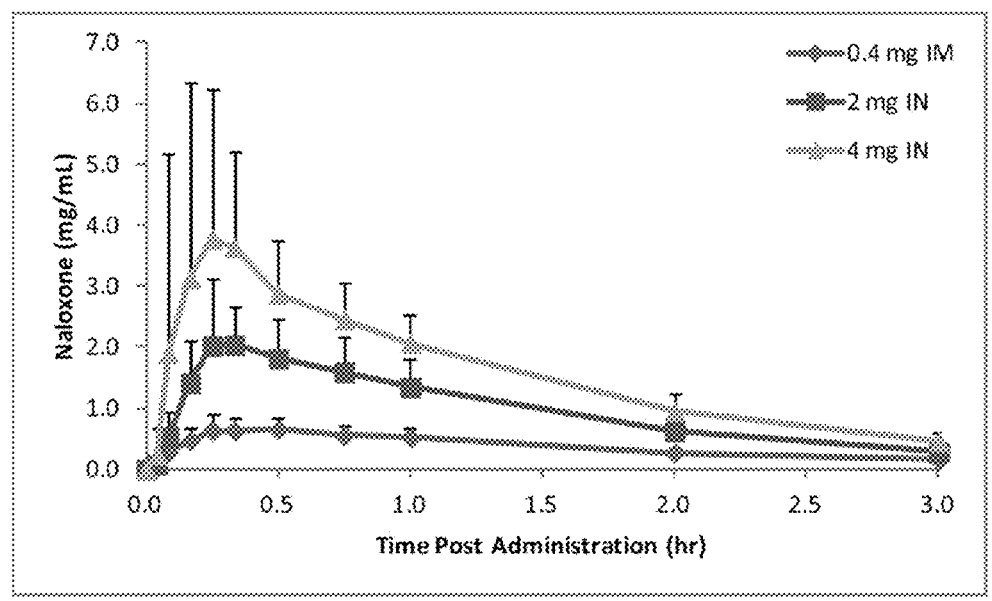
FIG. 1 shows the mean (±SD) naloxone plasma concentration following administration of 0.4 mg intramuscular (IM), 2 mg intranasal (IN), and 4 mg IN in 14 human subjects.
Figure 2:
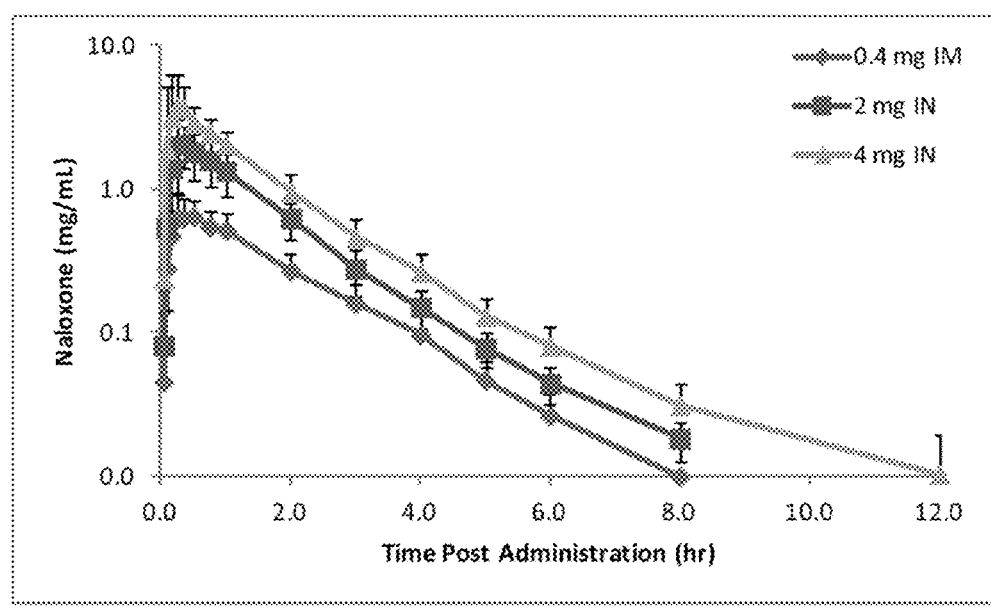
FIG. 2 shows the mean (±SD) naloxone plasma concentration with logarithmic transformation following administration of 0.4 mg intramuscular (IM), 2 mg intranasal (IN), and 4 mg IN in 14 human subjects.

For clarity and consistency, the following definitions will be used throughout this patent document.

The term "active ingredient" or "pharmaceutically active compound" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The term "actuation," as used herein, refers to operation of the device such that the pharmaceutical composition is delivered therefrom.

The term "agonist," as used herein, refers to as used herein refers to a moiety that interacts with and activates a receptor, and thereby initiates a physiological or pharmacological response characteristic of that receptor. The term "antagonist," as used herein, refers to a moiety that competitively binds to a receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist. The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist.

The term "antimicrobial preservative," as used herein, refers to a pharmaceutically acceptable excipient with antimicrobial properties which is added to a pharmaceutical composition to maintain microbiological stability.

The term "AUC," as used herein, refers to the area under the drug plasma concentration-time curve. The term "$AUC_{0-t}$," as used herein, refers to the area under the drug plasma concentration-time curve from t=0 to the last measurable concentration. The term "$AUC_{0-\infty}$," as used herein, refers to the area under the drug plasma concentration-time curve extrapolated to $\infty$. The term "$AUC_{0-t/D}$," as used herein, refers to the $AUC_{0-t}$ normalized to 0.4 mg IM naloxone. The term "$AUC_{0-\infty/D}$," as used herein, refers to the $AUC_{0-\infty}$ normalized to 0.4 mg IM naloxone The term "bioavailability (F)," as used herein, refers to the fraction of a dose of drug that is absorbed from its site of administration and reaches, in an unchanged form, the systemic circulation. The term "absolute bioavailability" is used when the fraction of absorbed drug is related to its IV bioavailability. It may be calculated using the following formula:

$$F = \frac{AUC_{extravascular}}{AUC_{intravenous}} \times \frac{Dose_{intravenous}}{Dose_{extravascular}}$$

The term relative bioavailability ($F_{rel}$) is used to compare two different extravascular routes of drug administration and it may be calculated using the following formula:

$$F_{rel} = \frac{AUC_{extravascular1}}{AUC_{extravascular2}} \times \frac{Dose_{extravascular2}}{Dose_{extravascular1}}$$

The term "clearance (CL)," as used herein, refers to the rate at which a drug is eliminated divided by its plasma concentration, giving a volume of plasma from which drug is completely removed per unit of time. CL is equal to the elimination rate constant ($\lambda$) multiplied by the volume of distribution ($V_d$), wherein "$V_d$" is the fluid volume that would be required to contain the amount of drug present in the body at the same concentration as in the plasma. The term "apparent clearance (CL/F)," as used herein, refers to clearance that does not take into account the bioavailability of the drug. It is the ratio of the dose over the AUC.

The term "$C_{max}$" as used herein, refers to the maximum observed plasma concentration. The term "$C_{max/D}$," as used herein, refers to $C_{max}$ normalized to 0.4 mg IM naloxone.

The term "coefficient of variation (CV)," as used herein, refers to the ratio of the sample standard deviation to the sample mean. It is often expressed as a percentage.

The term "confidence interval," as used herein, refers to a range of values which will include the true average value of a parameter a specified percentage of the time.

The term "device," as used herein, refers to an apparatus capable of delivering a drug to patient in need thereof.

The term "delivery time," as used herein, refers to the amount of time that elapses between a determination made by a healthcare professional, or an untrained individual that an individual is in need of nasal delivery of an opioid antagonist and completion of the delivery.

The term "elimination rate constant (λ)," as used herein, refers to the fractional rate of drug removal from the body. This rate is constant in first-order kinetics and is independent of drug concentration in the body. λ is the slope of the plasma concentration-time line (on a logarithmic y scale). The term "$\lambda_z$," as used herein, refers to the terminal phase elimination rate constant, wherein the "terminal phase" of the drug plasma concentration-time curve is a straight line when plotted on a semilogarithmic graph. The terminal phase is often called the "elimination phase" because the primary mechanism for decreasing drug concentration during the terminal phase is drug elimination from the body. The distinguishing characteristic of the terminal elimination phase is that the relative proportion of drug in the plasma and peripheral volumes of distribution remains constant. During this "terminal phase" drug returns from the rapid and slow distribution volumes to the plasma, and is permanently removed from the plasma by metabolism or renal excretion.

The term "equivalent," as used herein refers to a weight of an opioid antagonist selected from naloxone and pharmaceutically acceptable salts thereof that is equimolar to a specified weight of naloxone hydrochloride. For example, 8 mg of anhydrous naloxone hydrochloride (molecular weight, 363.84) is equivalent to about 7.2 mg of naloxone freebase (molecular weight, 327.37), and to about 8.8 mg of naloxone hydrochloride dihydrate (molecular weight 399.87).

The term "filled," as used herein, refers to an association between a device and a pharmaceutical composition, for example, when a pharmaceutical composition described herein comprising a therapeutically effective amount of an opioid antagonist is present within a reservoir that forms a part of a device described herein.

The term "hydrate," as used herein, refers to an opioid antagonist described herein or a salt thereof that further includes a stoichiometric or non-stoichiometric amount of water bound by non-covalent intermolecular forces.

The term "in need of treatment" and the term "in need thereof" when referring to treatment are used interchangeably and refer to a judgment made by a caregiver (e.g. physician, nurse, nurse practitioner, that a patient will benefit from treatment.

As used herein, two embodiments are "mutually exclusive" when one is defined to be something which is different than the other. For example, an embodiment wherein the amount of naloxone hydrochloride is specified to be 4 mg is mutually exclusive with an embodiment wherein the amount of naloxone hydrochloride is specified to be 2 mg. However, an embodiment wherein the amount of naloxone hydrochloride is specified to be 4 mg is not mutually exclusive with an embodiment in which less than about 10% of said pharmaceutical composition leaves the nasal cavity via drainage into the nasopharynx or externally.

The term "naloxone," as used herein, refers to a compound of the following structure:

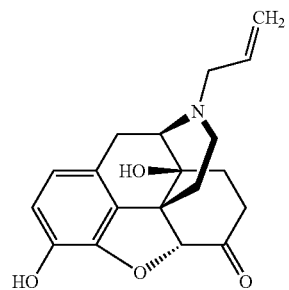

or a pharmaceutically acceptable salt, hydrate, or solvate thereof. The CAS registry number for naloxone is 465-65-6. Other names for naloxone include: 17-allyl-4,5a-epoxy-3,14-dihydroxymorphinan-6-one; (−)-17-allyl-4,5a-epoxy-3,14-dihydroxymorphinan-6-one; 4,5a-epoxy-3,14-dihydroxy-17-(2-propenyl)morphinan-6-one; and (−)-12-allyl-7,7a,8,9-tetrahydro-3,7a-dihydroxy-4aH-8,9c-iminoethanophenanthro[4,5-bcd]furan-5(6H)-one.

Naloxone hydrochloride may be anhydrous (CAS Reg. No. 357-08-4) and also forms a dihydrate (CAS No. 51481-60-8). It has been sold under various brand names including Narcan®, Nalone®, Nalossone®, Naloxona®, Naloxonum®, Narcanti®, and Narcon®.

The term "naltrexone," as used herein, refers to a compound of the following structure:

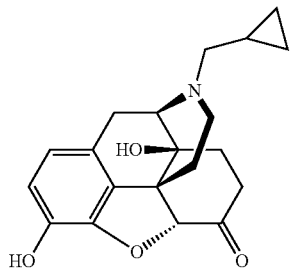

or a pharmaceutically acceptable salt, hydrate, or solvate thereof. The CAS registry number for naltrexone is 16590-41-3. Other names for naltrexone include: 17-(cyclopropylmethyl)-4,5a-epoxy-3,14-dihydroxymorphinan-6-one; (5α)-17-(cyclopropylmethyl)-3,14-dihydroxy-4,5-epoxymorphinan-6-one; and (1S,5R,13R,17S)-4-(cyclopropylmethyl)-10,17-dihydroxy-12-oxa-4-azapentacyclo[9.6.1.01,13.05,17.07,18]octadeca-7(18),8,10-trien-14-one.

Naltrexone hydrochloride (CAS Reg. No. 16676-29-2) has been marketed under the trade names Antaxone®, Depade®, Nalorex®, Revia®, Trexan®, Vivitrex®, and Vivitrol®.

The term "methylnaltrexone," as used herein, refers to a pharmaceutically acceptable salt comprising the cation (5α)-17-(cyclopropylmethyl)-3,14-dihydroxy-17-methyl-4,5-epoxymorphinanium-17-ium-6-one a compound of the following structure:

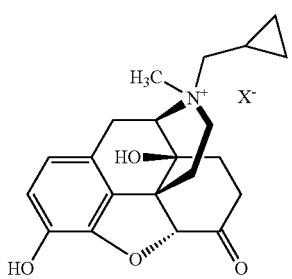

wherein X⁻ is a pharmaceutically acceptable anion. Methylnaltrexone bromide (CAS Reg. No. 75232-52-7) has been marketed under the trade name Relistor®.

The term "nalmefene," as used herein, refers to 17-cyclopropylmethyl-4,5a-epoxy-6-methylenemorphinan-3,14-diol, a compound of the following structure:

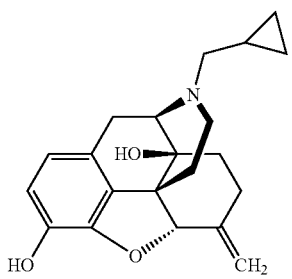

Nalmefene hydrochloride (CAS Reg. No. 58895-64-0) has been marketed under the trade names Nalmetrene®, Cervene®, Revex®, Arthrene®, and Incystene®.

The term "nostril," as used herein, is synonymous with "naris."

The term "opioid antagonist" includes, in addition to naloxone and pharmaceutically acceptable salts thereof: naltrexone, methylnaltrexone, and nalmefene, and pharmaceutically acceptable salts thereof. In some embodiments, the opioid antagonist is naloxone hydrochloride. In some embodiments, the opioid antagonist is naloxone hydrochloride dihydrate. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the nasally administering is accomplished using a device described herein.

The term "opioid overdose," as used herein, refers to an acute medical condition induced by excessive use of one or more opioids. Symptoms of opioid overdose include including respiratory depression (including postoperative opioid respiratory depression, acute lung injury, and aspiration pneumonia), central nervous system depression (which may include sedation, altered level consciousness, miotic (constricted) pupils), and cardiovascular depression (which may include hypoxemia and hypotension). Visible signs of opioid overdose or suspected opioid overdose include: unresponsiveness and/or loss of consciousness (won't respond to stimuli such as shouting, shaking, or rubbing knuckles on sternum); slow, erratic, or stopped breathing; slow, erratic, or stopped pulse; deep snoring or choking/gurgling sounds; blue or purple fingernails or lips; pale and/or clammy face; slack or limp muscle tone; contracted pupils; and vomiting. Because opioid overdose may be difficult to diagnose and/or quantify, particularly by a lay person, as used herein, treatment of opioid overdose is meant to include treatment of suspected opioid overdose in opioid-intoxicated patients. Opioids that may induce overdose include, codeine, morphine, methadone, fentanyl, oxycodone HCl, hydrocodone bitartrate, hydromorphone, oxymorphone, meperidine, propoxyphene, opium, heroin, tramadol, tapentadol, and certain narcotic-antagonist analgesics, such as, nalbuphine, pentazocine and butorphanol. In some embodiments, the opioid agonist is in a tamper-proof formulation. In some embodiments, the opioid agonist is in a tamper-resistant formulation. In some embodiments, the opioid agonist is selected from Acurox® Oxycodone DETERx®, Egalet hydrocodone, Egalet morphine, Egalet oxycodone, Exalgo®, Opana®, and Remoxy®.

The term "patient," as used herein, refers to any subject (preferably human) afflicted with a condition likely to benefit from a treatment with a therapeutically effective amount of an opioid antagonist.

The terms "permeation enhancer" and "penetration enhancer," as disclosed herein, are intended to be equivalent, both referring to an agent which aids in absorption of a compound, such as through the nasal mucosa.

The term "pharmaceutical composition," as used herein, refers to a composition comprising at least one active ingredient; including but not limited to, salts, solvates and hydrates of the opioid antagonists described herein, whereby the composition is amenable to use for a specified, efficacious outcome in a mammal (for example, without limitation, a human).

The term "pre-primed," as used herein, refers to a device, such as a nasal spray which is capable of delivering a pharmaceutical composition to a patient in need thereof with the first actuation of the spray pump, i.e., without the need to prime the pump prior to dosing, such as by actuating the pump one or more times until a spray appears.

The term "prone," as used herein, refers to a patient who is lying face down.

The term "receptor binding or occupancy" refers to a characterization of the kinetics between a radioactive drug and receptors or other binding sites throughout the body, and characterization of the radioactive drug binding affinity to these receptors.

The term "recovery position," as used herein, means a position of the human body in which a patient lies on his/her side, with a leg or knee out in front (e.g., to prevent rolling onto his/her stomach) and at least one hand supporting the head (e.g., to elevate the face to facilitate breathing and prevent inhalation of vomit).

The term "solvate," as used herein, refers to an opioid antagonist described herein or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "sterile filling," as used herein, refers methods of manufacturing the devices and pharmaceutical compositions described herein, such that the use of preservatives is not required. Sterile drug products may be produced using aseptic processing or terminal sterilization. Terminal sterilization usually involves filling and sealing product containers under high-quality environmental conditions. In an aseptic process, the drug product, container, and closure are first subjected to sterilization methods separately, as appropriate, and then brought together.

The term "storage-stable," as used herein, refers to a pharmaceutical composition in which at least about 95% to 99.5% of the active ingredient remains in an undegraded state after storage of the pharmaceutical composition at specified temperature and humidity for a specified time, for example, for 12 months at 25° C. and 60% relative humidity.

The term "supine," as used herein, refers to a patient who is lying face up.

The term "$t_{1/2}$" or "half-life," as used herein, refers to the amount of time required for half of a drug to be eliminated from the body or the time required for a drug concentration to decline by half.

The term "tonicity agent," as used herein, refers to a compound which modifies the osmolality of a formulation, for example, to render it isotonic. Tonicity agents include, dextrose, lactose, sodium chloride, calcium chloride, magnesium chloride, sorbitol, sucrose, mannitol, trehalose, raffinose, polyethylene glycol, hydroxyethyl starch, glycine and the like.

The term "tomography," as used herein, refers to a process of imaging by sections. The images may be looked at individually, as a series of two-dimensional slices or together, as a computer-generated three-dimensional representation.

The term "pharmaceutically acceptable," as used herein, refers to a component of a pharmaceutical composition that it compatible with the other ingredients of the formulation and not overly deleterious to the recipient thereof.

The term "substantially free of antimicrobial preservatives" is understood by one of ordinary skill in the art to described a pharmaceutical composition that may comprise less than 1% w/w antimicrobial preservatives.

The term "therapeutically effective amount," as used herein, refers to the amount of active compound or pharmaceutical agent that elicits the biological or medicinal response in a tissue, system, or individual that is being sought by a researcher, healthcare provider or individual.

The term "$T_{max}$," as used herein, refers to the time from administration of the pharmaceutical compositions described herein to maximum drug plasma concentration.

The term "untrained individual" refers to an individual administering to patient an opioid antagonist using a device described herein, wherein the individual is not a healthcare professional and has received no training in the use of the device, such as through an overdose education and nasal naloxone distribution (OEND) program.

Opioid Antagonists

Provided are drug products adapted for nasal delivery of an opioid receptor antagonist. Opioid receptor antagonists are a well recognized class of chemical agents. They have been described in detail in the scientific and patent literature. Pure opioid antagonists, such as naloxone, are agents which specifically reverse the effects of opioid agonists but have no opioid agonist activity.

Naloxone is commercially available as a hydrochloride salt. Naloxone hydrochloride (17-allyl-4,5a-epoxy-3,14-dihydroxymorphinan-6-one hydrochloride), a narcotic antagonist, is a synthetic congener of oxymorphone. In structure it differs from oxymorphone in that the methyl group on the nitrogen atom is replaced by an allyl group. Naloxone hydrochloride is an essentially pure narcotic antagonist, i.e., it does not possess the "agonistic" or morphine-like properties characteristic of other narcotic antagonists; naloxone does not produce respiratory depression, psychotomimetic effects or pupillary constriction. In the absence of narcotics or agonistic effects of other narcotic antagonists it exhibits essentially no pharmacologic activity. Naloxone has not been shown to produce tolerance or to cause physical or psychological dependence. In the presence of physical dependence on narcotics naloxone will produce withdrawal symptoms.

While the mechanism of action of naloxone is not fully understood, the preponderance of evidence suggests that naloxone antagonizes the opioid effects by competing for the same receptor sites. When naloxone hydrochloride is administered intravenously the onset of action is generally apparent within two minutes; the onset of action is only slightly less rapid when it is administered subcutaneously or intramuscularly. The duration of action is dependent upon the dose and route of administration of naloxone hydrochloride. Intramuscular administration produces a more prolonged effect than intravenous administration. The requirement for repeat doses of naloxone, however, will also be dependent upon the amount, type and route of administration of the narcotic being antagonized. Following parenteral administration naloxone hydrochloride is rapidly distributed in the body. It is metabolized in the liver, primarily by glucuronide conjugation, and excreted in urine. In one study the serum half-life in adults ranged from 30 to 81 minutes (mean 64±12 minutes). In a neonatal study the mean plasma half-life was observed to be 3.1±0.5 hours.

Provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride. Also provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride. In some embodiments, the therapeutically effective amount is equivalent to about 2 mg to about 24 mg of naloxone hydrochloride. In some embodiments, the therapeutically effective amount is equivalent to about 2 mg to about 12 mg of naloxone hydrochloride. In some embodiments, the therapeutically effective amount is equivalent to about 3 mg to about 18 mg of naloxone hydrochloride. In some embodiments, the therapeutically effective amount is equivalent to about 4 mg to about 10 mg of naloxone hydrochloride. In some embodiments, the therapeutically effective amount is equivalent to about 5 mg to about 11 mg of naloxone hydrochloride. In some embodiments, the therapeutically effective amount is equivalent to about 6 mg to about 10 mg of naloxone hydrochloride. In some embodiments, the therapeutically effective amount is equivalent to about 4 mg to about 8 mg of naloxone hydrochloride. In some embodiments, the therapeutically effective amount is equivalent to about 7 mg to about 9 mg of naloxone hydrochloride. In some embodiments, the therapeutically effective amount is equivalent to about 3.4 mg of naloxone hydrochloride. In some embodiments, the therapeutically effective amount is equivalent to about 4 mg of naloxone hydrochloride. In some embodiments, the therapeutically effective amount is equivalent to about 5 mg of naloxone hydrochloride. In some embodiments, the therapeutically effective amount is equivalent to about 6 mg of naloxone hydrochloride. In some embodiments, the therapeutically effective amount is equivalent to about 7 mg of naloxone hydrochloride. In some embodiments, the therapeutically effective amount is equivalent to about 8 mg of naloxone hydrochloride. In some embodiments, the therapeutically effective amount is equivalent to about 9 mg of naloxone hydrochloride. In some embodiments, the therapeutically effective amount is equivalent to about 10 mg of naloxone hydrochloride. In some embodiments, the therapeutically effective amount is equivalent to about 11 mg of naloxone hydrochloride. In some embodiments, the therapeutically effective amount is equivalent to about 12 mg of naloxone hydrochloride. In some embodiments, the opioid antagonist is the only pharmaceutically active compound in pharmaceutical composition. In some embodiments, the opioid antagonist is naloxone hydrochloride. In some embodiments, the opioid antagonist is anhydrous naloxone hydrochloride. In some embodiments, the opioid antagonist is naloxone hydrochloride dihydrate.

While many of the embodiments of the pharmaceutical compositions described herein will be described and exemplified with naloxone, other opioid antagonists can be adapted for nasal delivery based on the teachings of the specification. In fact, it should be readily apparent to one of ordinary skill in the art from the teachings herein that the devices and pharmaceutical compositions described herein may be suitable for other opioid antagonists. The opioid receptor antagonists described herein include μ-opioid antagonists and δ-opioid receptor antagonists. Examples of useful opioid receptor antagonists include naloxone, naltrexone, methylnaltrexone, and nalmefene. Other useful opioid receptor antagonists are known (see, e.g., Kreek et al., U.S. Pat. No. 4,987,136).

Also provided are devices adapted for nasal delivery of a pharmaceutical composition to a patient, comprising a therapeutically effective amount of an opioid antagonist, wherein the device is pre-primed, and wherein the therapeutically effective amount is about 4 mg to about 12 mg. In some embodiments, the therapeutically effective amount is equivalent to about 3.4 mg of naloxone hydrochloride. In some embodiments, the therapeutically effective amount is equivalent to about 4 mg of naloxone hydrochloride. In some embodiments, the opioid antagonist is selected from naltrexone, methylnaltrexone, and nalmefene, and pharmaceutically acceptable salts thereof. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the opioid antagonist is the only pharmaceutically active compound in pharmaceutical composition.

Nasal Drug Delivery Devices and Kits

Also provided are nasal drug delivery devices comprising a pharmaceutical composition described herein. Nasal delivery is considered an attractive route for needle-free, systemic drug delivery, especially when rapid absorption and effect are desired. In addition, nasal delivery may help address issues related to poor bioavailability, slow absorption, drug degradation, and adverse events (AEs) in the gastrointestinal tract and avoids the first-pass metabolism in the liver.

Liquid nasal formulations are mainly aqueous solutions, but suspensions and emulsions can also be delivered. In traditional spray pump systems, antimicrobial preservatives are typically required to maintain microbiological stability in liquid formulations.

Some EMS programs have developed a system using existing technologies of an approved drug and an existing medical device to administer naloxone intranasally, albeit in a non-FDA approved manner. This has been accomplished by using the injectable formulation (1 mg/mL) and administering 1 mL per nostril via a marketed nasal atomizer/nebulizer device. The system combines an FDA-approved naloxone injection product (with a Luer fitted tip, no needles) with a marketed, medical device called the Mucosal Atomization Device (MAD™ Nasal, Wolfe Tory Medical, Inc.). This initiative is consistent with the U.S. Needlestick Safety and Prevention Act (Public Law 106-430). The EMS programs recognize limitations of this system, one limitation being that it is not assembled and ready-to-use. Although this administration mode appears to be effective in reversing narcosis, the formulation is not concentrated for retention in the nasal cavity. The 1 mL delivery volume per nostril is larger than that generally utilized for intranasal drug administration. Therefore, there is loss of drug from the nasal cavity, due either to drainage into the nasopharynx or externally from the nasal cavity. The devices described herein are improved ready-to-use products specifically optimized, concentrated, and formulated for nasal delivery.

Metered spray pumps have dominated the nasal drug delivery market since they were introduced. The pumps typically deliver 100 μL (25-200 μL) per spray, and they offer high reproducibility of the emitted dose and plume geometry in in vitro tests. The particle size and plume geometry can vary within certain limits and depend on the properties of the pump, the formulation, the orifice of the actuator, and the force applied. Traditional spray pumps replace the emitted liquid with air, and preservatives are therefore required to prevent contamination. However, driven by the studies suggesting possible negative effects of preservatives, pump manufacturers have developed different spray systems that avoid the need for preservatives. These systems use a collapsible bag, a movable piston, or a compressed gas to compensate for the emitted liquid volume (www.aptar.com and www.rexam.-com). The solutions with a collapsible bag and a movable piston compensating for the emitted liquid volume offer the additional advantage that they can be emitted upside down, without the risk of sucking air into the dip tube and compromising the subsequent spray. This may be useful for some products where the patients are bedridden and where a headdown application is recommended. Another method used for avoiding preservatives is that the air that replaces the emitted liquid is filtered through an aseptic air filter. In addition, some systems have a ball valve at the tip to prevent contamination of the liquid inside the applicator tip (www.aptar.com). More recently, pumps have been designed with side-actuation and introduced for delivery of fluticasone furoate for the indication of seasonal and perennial allergic rhinitis. The pump was designed with a shorter tip to avoid contact with the sensitive mucosal surfaces. New designs to reduce the need for priming and re-priming, and pumps incorporating pressure point features to improve the dose reproducibility and dose counters and lock-out mechanisms for enhanced dose control and safety are available (www.rexam.com and www.aptar.com).

Metered-dose spray pumps require priming and some degree of overfill to maintain dose conformity for the labeled number of doses. They are well suited for drugs to be administered daily over a prolonged duration, but due to the priming procedure and limited control of dosing, they are less suited for drugs with a narrow therapeutic window. For expensive drugs and vaccines intended for single administration or sporadic use and where tight control of the dose and formulation is of particular importance, single-dose or bi-dose spray devices are preferred (www.aptar.com). A simple variant of a single-dose spray device (MAD™) is offered by LMA (LMA, Salt Lake City, Utah, USA; www.l-mana. com). A nosepiece with a spray tip is fitted to a standard syringe. The liquid drug to be delivered is first drawn into the syringe and then the spray tip is fitted onto the syringe. This device has been used in academic studies to deliver, for example, a topical steroid in patients with chronic rhinosinusitis and in a vaccine study. A pre-filled device based on the same principle for one or two doses (Accuspray™, Becton Dickinson Technologies, Research Triangle Park, N.C., USA; www.bdpharma.com) is used to deliver the influenza vaccine FluMist (www.flumist.com), approved for both adults and children in the US market. A similar device for two doses was marketed by a Swiss company for delivery of another influenza vaccine a decade ago. The single- and bi-dose devices mentioned above consist of a reservoir, a piston, and a swirl chamber (see, e.g., the UDS UnitDose and BDS BiDose devices from Aptar, formerly Pfeiffer). The spray is formed when the liquid is forced out through the swirl chamber. These devices are held between the second and the third fingers with the thumb on the actuator. A pressure point mechanism incorporated in some devices secures reproducibility of the actuation force and emitted plume characteristics. Currently, marketed nasal migraine drugs like Imitrex (www.gsk.com) and Zomig (www.az.com; Pfeiffer/Aptar single-dose device) and the marketed influenza vaccine Flu-Mist (www.flumist.com; Becton Dickinson single-dose spray device) are delivered with this type of device.

With sterile filling, the use of preservatives is not required, but overfill is required resulting in a waste fraction similar to the metered-dose, multi-dose sprays. To emit 100 µL, a volume of 125 µL is filled in the device (Pfeiffer/Aptar single-dose device) used for the intranasal migraine medications Imitrex (sumatriptan) and Zomig (zolmitriptan) and about half of that for a bi-dose design. Sterile drug products may be produced using aseptic processing or terminal sterilization. Terminal sterilization usually involves filling and sealing product containers under high-quality environmental conditions. Products are filled and sealed in this type of environment to minimize the microbial and particulate content of the in-process product and to help ensure that the subsequent sterilization process is successful. In most cases, the product, container, and closure have low bioburden, but they are not sterile. The product in its final container is then subjected to a sterilization process such as heat or irradiation. In an aseptic process, the drug product, container, and closure are first subjected to sterilization methods separately, as appropriate, and then brought together. Because there is no process to sterilize the product in its final container, it is critical that containers be filled and sealed in an extremely high-quality environment. Aseptic processing involves more variables than terminal sterilization. Before aseptic assembly into a final product, the individual parts of the final product are generally subjected to various sterilization processes. For example, glass containers are subjected to dry heat; rubber closures are subjected to moist heat; and liquid dosage forms are subjected to filtration. Each of these manufacturing processes requires validation and control.

Accordingly, provided herein are devices adapted for nasal delivery of a pharmaceutical composition to a patient, comprising a therapeutically effective amount of an opioid antagonist selected from naloxone and pharmaceutically acceptable salts thereof, wherein said device is pre-primed, and wherein said therapeutically effective amount, is equivalent to about 2 mg to about 12 mg of naloxone hydrochloride.

In some embodiments, said opioid antagonist is naloxone hydrochloride. In some embodiments, said opioid antagonist is naloxone hydrochloride dihydrate.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

In some embodiments, said therapeutically effective amount is equivalent to about 4 mg to about 10 mg of naloxone hydrochloride. In some embodiments, said therapeutically effective amount is equivalent to an amount chosen from about 2 mg naloxone hydrochloride, about 4 mg of naloxone hydrochloride, and about 8 mg naloxone hydrochloride. In some embodiments, said therapeutically effective amount is equivalent to about 2 mg of naloxone hydrochloride. In some embodiments, said therapeutically effective amount is equivalent to about 4 mg of naloxone hydrochloride. In some embodiments, said therapeutically effective amount is equivalent to about 8 mg of naloxone hydrochloride. In some embodiments, the therapeutically effective amount is equivalent to about 3.4 mg of naloxone hydrochloride.

In some embodiments, said therapeutically effective amount is about 2.2 mg to about 13.2 mg of naloxone hydrochloride dihydrate. In some embodiments, said therapeutically effective amount is about 4.4 mg to about 11 mg of naloxone hydrochloride dihydrate. In some embodiments, said therapeutically effective amount is an amount chosen from about 2.2 mg naloxone hydrochloride dihydrate, about 4.4 mg of naloxone hydrochloride dihydrate, and about 8.8 mg naloxone hydrochloride dihydrate. In some embodiments, said therapeutically effective amount is about 2.2 mg of naloxone hydrochloride dihydrate. In some embodiments, said therapeutically effective amount is about 4.4 mg of naloxone hydrochloride dihydrate. In some embodiments, said therapeutically effective amount is about 8.8 mg of naloxone hydrochloride dihydrate.

In some embodiments, said opioid antagonist is the only pharmaceutically active compound in said pharmaceutical composition.

In some embodiments, said pharmaceutical composition comprises a solution of naloxone hydrochloride, or a hydrate thereof.

In some embodiments, the volume of said pharmaceutical composition in said reservoir is not more than about 140 µL.

In some embodiments, about 100 µL of said pharmaceutical composition in said reservoir is delivered to said patient in one actuation.

In some embodiments, said pharmaceutical composition further comprises one or more excipients selected from water and NaCl.

In some embodiments, said pharmaceutical composition is substantially free of antimicrobial preservatives.

In some embodiments, said pharmaceutical composition comprises a compound which is a preservative, cationic surfactant, and/or permeation/penetration enhancer.

In certain embodiments, said pharmaceutical composition comprises benzalkonium chloride. The benzalkonium chloride can function as a preservative (even in low amounts), a permeation/penetration enhancer, and/or a cationic surfactant (typically at a higher amount for these latter two). Benzalkonium chloride is represented by the following structure:

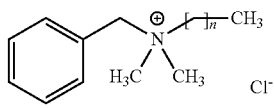

in which n is an integer, and a mixture of more than one thereof can be used. In certain embodiments, n is 8, 10, 12, 14, 16, or 18.

In some embodiments, said pharmaceutical composition further comprises one or more excipients selected from water, NaCl, benzalkonium chloride, sodium edetate, disodium edetate, and hydrochloric acid.

In some embodiments, said pharmaceutical composition further comprises water, NaCl, benzalkonium chloride, disodium edetate, and hydrochloric acid.

In some embodiments, said pharmaceutical composition further comprises:
an isotonicity agent;
a preservative;
a stabilizing agent;
an amount of an acid sufficient to achieve a pH or 3.5-5.5; and
an amount of water sufficient to achieve a final volume of about 100 µL.

In some embodiments, said pharmaceutical composition comprises:
between about 0.2 mg and about 1.2 mg of an isotonicity agent;
between about 0.005 mg and about 0.015 mg of a compound which is a preservative, cationic surfactant, and/or permeation enhancer;
between about 0.1 mg and about 0.5 mg of a stabilizing agent;
an amount of an acid sufficient to achieve a pH or 3.5-5.5; and
an amount of water sufficient to achieve a final volume of about 100 µL.

In some embodiments,
the isotonicity agent is NaCl;
the compound which is a preservative, cationic surfactant, and/or permeation enhancer is benzalkonium chloride;
the stabilizing agent is disodium edetate; and
the acid is hydrochloric acid.

In some embodiments, said pharmaceutical composition comprises:
about 0.74 mg NaCl;
about 0.01 mg benzalkonium chloride;
about 0.2 mg disodium edetate;
an amount of hydrochloric acid sufficient to achieve a pH or 3.5-5.5; and
an amount of water sufficient to achieve a final volume of about 100 µL.

In some embodiments, said device is filled with said pharmaceutical composition using sterile filling.

In some embodiments, said pharmaceutical composition is storage-stable for about twelve months at about 25° C. and about 60% relative humidity.

In some embodiments, said device is a single-dose device, wherein said pharmaceutical composition is present in one reservoir, and wherein said therapeutically effective amount of said opioid antagonist is delivered essentially by one actuation of said device into one nostril of said patient.

In some embodiments, about 100 µL of said pharmaceutical composition is delivered by said actuation.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $T_{max}$ of less than 30 minutes. In some embodiments, the plasma concentration versus time curve of said opioid antagonist in said patient has a $T_{max}$ of less than 25 minutes. In some embodiments, the plasma concentration versus time curve of the opioid antagonist in the patient has a $T_{max}$ of less than 20 minutes. In some embodiments, the plasma concentration versus time curve of said opioid antagonist in said patient has a $T_{max}$ of about 20 minutes. In some embodiments, the plasma concentration versus time curve of the opioid antagonist in the patient has a $T_{max}$ of less than 19 minutes. In some embodiments, the plasma concentration versus time curve of the opioid antagonist in the patient has a $T_{max}$ of about 18.5 minutes.

In some embodiments, delivery of said therapeutically effective amount to said patient, provides occupancy at $T_{max}$ of said opioid antagonist at the opioid receptors in the respiratory control center of said patient of greater than about 90%. In some embodiments, delivery of said therapeutically effective amount to said patient, provides occupancy at $T_{max}$ of said opioid antagonist at the opioid receptors in the respiratory control center of said patient of greater than about 95%. In some embodiments, delivery of said therapeutically effective amount to said patient, provides occupancy at $T_{max}$ of said opioid antagonist at the opioid receptors in the respiratory control center of said patient of greater than about 99%.

In some embodiments, said patient is free from respiratory depression for at least about 1 hour following treatment comprising essentially of delivery of said therapeutically effective amount of said opioid antagonist. In some embodiments, said patient is free from respiratory depression for at least about 2 hours following treatment comprising essentially of delivery of said therapeutically effective amount of said opioid antagonist. In some embodiments, said patient is free from respiratory depression for at least about 4 hours following treatment comprising essentially of delivery of said therapeutically effective amount of said opioid antagonist. In some embodiments, said patient is free from respiratory depression for at least about 6 hours following treatment comprising essentially of delivery of said therapeutically effective amount of said opioid antagonist.

In some embodiments, said device is a bi-dose device, wherein a first volume of said pharmaceutical composition is present in a first reservoir and a second volume of said pharmaceutical composition is present in a second reservoir, and wherein said therapeutically effective amount is delivered essentially by a first actuation of said device into a first nostril of said patient and a second actuation of said device into a second nostril of said patient.

In some embodiments, said first volume and said second volume combined is equal to not more than about 380 µL.

In some embodiments, about 100 µL of said first volume of said pharmaceutical composition is delivered by said first actuation.

In some embodiments, about 100 µL of said second volume of said pharmaceutical composition is delivered by said second actuation.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $T_{max}$ of less than 30 minutes. In some embodiments, the plasma concentration versus time curve of said opioid antagonist in said patient has a $T_{max}$ of less than 25 minutes. In some embodiments, the plasma concentration versus time curve of said opioid antagonist in said patient has a $T_{max}$ of about 20 minutes. In some embodiments, the plasma concentration versus time curve of the opioid antagonist in the patient has a $T_{max}$ of less than 19 minutes. In some embodiments, the plasma concentration versus time curve of the opioid antagonist in the patient has a $T_{max}$ of about 18.5 minutes.

In some embodiments, delivery of said therapeutically effective amount to said patient, provides occupancy at $T_{max}$ of said opioid antagonist at the opioid receptors in the respiratory control center of said patient of greater than about 90%. In some embodiments, delivery of said therapeutically effective amount to said patient, provides occupancy at $T_{max}$ of said opioid antagonist at the opioid receptors in the respiratory control center of said patient of greater than about 95%. In some embodiments, delivery of said therapeutically effective amount to said patient, provides occupancy at $T_{max}$ of said opioid antagonist at the opioid receptors in the respiratory control center of said patient of greater than about 99%.

In some embodiments, said patient is free from respiratory depression for at least about 1 hour following treatment comprising essentially of delivery of said therapeutically effective amount of said opioid antagonist. In some embodiments, said patient is free from respiratory depression for at least about 2 hours following treatment comprising essentially of delivery of said therapeutically effective amount of said opioid antagonist. In some embodiments, said patient is free from respiratory depression for at least about 4 hours following treatment comprising essentially of delivery of said therapeutically effective amount of said opioid antagonist. In some embodiments, said patient is free from respiratory depression for at least about 6 hours following treatment comprising essentially of delivery of said therapeutically effective amount of said opioid antagonist.

Also provided herein is a single-use, pre-primed device adapted for nasal delivery of a pharmaceutical composition to a patient by one actuation of said device into one nostril of said patient, having a single reservoir comprising about 100 µL of a pharmaceutical composition which is an aqueous solution comprising:

about 2 mg or about 4 mg naloxone hydrochloride or a hydrate thereof;
between about 0.2 mg and about 1.2 mg of an isotonicity agent;
between about 0.005 mg and about 0.015 mg of a compound which is a preservative, cationic surfactant, and/or permeation enhancer;
between about 0.1 mg and about 0.5 mg of a stabilizing agent;
an amount of an acid sufficient to achieve a pH or 3.5-5.5.

In some embodiments, the device comprises about 4 mg naloxone hydrochloride or a hydrate thereof. In some embodiments, the device comprises about 2 mg naloxone hydrochloride or a hydrate thereof. In some embodiments, the device comprises about 4.4 mg naloxone hydrochloride dihydrate. In some embodiments, the device comprises about 2.2 mg naloxone hydrochloride dihydrate.

In some embodiments,
the isotonicity agent is NaCl;
the compound which is a preservative, cationic surfactant, and/or permeation enhancer is benzalkonium chloride;
the stabilizing agent is disodium edetate; and
the acid is hydrochloric acid.

In some embodiments, the device comprises:
about 2.2 mg or about 4.4 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH or 3.5-5.5.

In some embodiments, the device comprises about 4.4 mg naloxone hydrochloride dihydrate. In some embodiments, the device comprises about 2.2 mg naloxone hydrochloride dihydrate.

In some embodiments, upon nasal delivery of said pharmaceutical composition to said patient, less than about 10% of said pharmaceutical composition leaves the nasal cavity via drainage into the nasopharynx or externally.

In some embodiments, the plasma concentration versus time curve of said naloxone hydrochloride in said patient has a $T_{max}$ of between about 20 and about 30 minutes.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $T_{max}$ of less than 30 minutes. In some embodiments, the plasma concentration versus time curve of said opioid antagonist in said patient has a $T_{max}$ of less than 25 minutes. In some embodiments, the plasma concentration versus time curve of said opioid antagonist in said patient has a $T_{max}$ of about 20 minutes. In some embodiments, the plasma concentration versus time curve of the opioid antagonist in the patient has a $T_{max}$ of less than 19 minutes. In some embodiments, the plasma concentration versus time curve of the opioid antagonist in the patient has a $T_{max}$ of about 18.5 minutes.

In some embodiments, delivery of said therapeutically effective amount to said patient, provides occupancy at $T_{max}$ of said opioid antagonist at the opioid receptors in the respiratory control center of said patient of greater than about 90%. In some embodiments, delivery of said therapeutically effective amount to said patient, provides occupancy at $T_{max}$ of said opioid antagonist at the opioid receptors in the respiratory control center of said patient of greater than about 95%. In some embodiments, delivery of said therapeutically effective amount to said patient, provides occupancy at $T_{max}$ of said opioid antagonist at the opioid receptors in the respiratory control center of said patient of greater than about 99%.

In some embodiments, said patient is free from respiratory depression for at least about 1 hour following treatment comprising essentially of delivery of said therapeutically effective amount of said opioid antagonist. In some embodiments, said patient is free from respiratory depression for at least about 2 hours following treatment comprising essentially of delivery of said therapeutically effective amount of said opioid antagonist. In some embodiments, said patient is free from respiratory depression for at least about 4 hours following treatment comprising essentially of delivery of said therapeutically effective amount of said opioid antagonist. In some embodiments, said patient is free from respiratory depression for at least about 6 hours following treatment comprising essentially of delivery of said therapeutically effective amount of said opioid antagonist.

In some embodiments, said device is filled with said pharmaceutical composition using sterile filling.

In some embodiments, said pharmaceutical composition is storage-stable for about twelve months at about 25° C. and about 60% relative humidity.

In some embodiments, said opioid antagonist is the only pharmaceutically active compound in said pharmaceutical composition.

Also provided are devices as recited in any of the preceding embodiments for use in the treatment of an opioid overdose symptom selected from: respiratory depression, postoperative opioid respiratory depression, altered level consciousness, miotic pupils, cardiovascular depression, hypoxemia, acute lung injury, aspiration pneumonia, sedation, and hypotension.

Also provided are devices as recited in any of the preceding embodiments for use in the reversal of respiratory depression induced by opioids.

In some embodiments, said respiratory depression is caused by the illicit use of opioids or by an accidental misuse of opioids during medical opioid therapy.

Also provided are devices as recited in any of the preceding embodiments for use in the complete or partial reversal of narcotic depression, including respiratory depression, induced by opioids selected from: natural and synthetic narcotics, propoxyphene, methadone, nalbuphine, pentazocine and butorphanol.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

Also provided are kits comprising a device described herein and written instructions for using the device. Also provided are kits comprising a device described herein and an opioid agonist. In some embodiments the kit further comprises written instructions. In some embodiments, the opioid agonist is selected from codeine, morphine, methadone, fentanyl, oxycodone HCl, hydrocodone bitartrate, hydromorphone, oxymorphone, meperidine, propoxyphene, opium, heroin, and certain narcotic-antagonist analgesics, such as, nalbuphine, pentazocine and butorphanol. In some embodiments, the opioid agonist is selected from tapentadol and tramadol.

Also provided are embodiments wherein any embodiment above may be combined with any one or more of these embodiments, provided the combination is not mutually exclusive.

Tamper-proof and tamper-resistant formulating technologies have been developed for safer delivery of opioid antagonists, but such formulations are still abused resulting in opioid overdose. One such technology (Abuse Deterrent Prolonged Release Erosion Matrix (ADPREM); Egalet) utilizes a water-degradable polymer matrix technology that erodes from the surface at a constant rate. The matrix consists of one or more plasticizing polymers that cannot be crushed or melted. Another such technology (Abuse Resistant Technology (ART); Elite Laboratories) utilizes a proprietary coating technology consisting of various polymers that can sequester an opioid antagonist (naltrexone) in fragile micropellets that are indistinguishable from the pellets containing the opioid. The formulation is designed to release sequestered antagonist only if the dosage is crushed or otherwise damaged for extraction. Oral dosage forms are prepared by coating powders, crystals, granules, or pellets with various polymers to impart different characteristics. The formulations can release the active drug in both immediate and sustained release form. Chronodelivery formulations using this technology can effectively delay drug absorption for up to five hours. Aversion (Acura Pharmaceuticals) utilizes certain proprietary combinations of functional excipients (e.g., gelling agents) and active ingredients intended to discourage the most common methods of prescription drug misuse and abuse. Ingredients may include nasal irritants (e.g., capsaicin) and aversive agents (e.g., niacin). In some embodiments, the opioid agonist is in a tamper-proof formulation. In some embodiments, the opioid agonist is in a tamper-resistant formulation. In some embodiments, the opioid agonist is selected from Acurox® Oxycodone DETERx®, Egalet hydrocodone, Egalet morphine, Egalet oxycodone, Exalgo®, Opana®, and Remoxy®.

Pharmaceutical Compositions

Also provided are pharmaceutical compositions comprising one or more opioid antagonist. In some embodiments the pharmaceutical compositions comprise an opioid antagonist and a pharmaceutically acceptable carrier. The carrier(s) must be "acceptable" in the sense of being compatible with the other ingredients of the formulation and not overly deleterious to the recipient thereof. Some embodiments of the present invention include a method of producing a pharmaceutical composition comprising admixing at least one opioid antagonist and a pharmaceutically acceptable carrier. Pharmaceutical compositions are applied directly to the nasal cavity using the devices described herein. In the case of a spray, this may be achieved for example by means of a metering atomizing spray pump.

Liquid preparations include solutions, suspensions and emulsions, for example, water or water-propylene glycol solutions. Additional ingredients in liquid preparations may include: antimicrobial preservatives, such as benzalkonium chloride (which may also act as a cationic surfactant and/or a permeation enhancer), methylparaben, sodium benzoate, benzoic acid, phenyl ethyl alcohol, and the like, and mixtures thereof; surfactants such as Polysorbate 80 NF, polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene (5) sorbitan monooleate, polyoxyethylene 20 sorbitan trioleate, polyoxyethylene 20 sorbitan monoisostearate, sorbitan monooleate, sorbitan monolaurate, sorbitan monopalmitate, sorbitan monostearate, sorbitan trilaurate, sorbitan trioleate, sorbitan tristearate, and the like, and mixtures thereof; a tonicity agent such as: dextrose, lactose, sodium chloride, calcium chloride, magnesium chloride, sorbitol, sucrose, mannitol, trehalose, raffinose, polyethylene glycol, hydroxyethyl starch, glycine, and the like, and mixtures thereof; and a suspending agent such as microcrystalline cellulose, carboxymethylcellulose sodium NF, polyacrylic acid, magnesium aluminum silicate, xanthan gum, and the like, and mixtures thereof.

The opioid antagonists described herein can be formulated into pharmaceutical compositions using techniques well known to those in the art. Suitable pharmaceutically acceptable carriers, outside those mentioned herein, are known in the art; for example, see Remington: The Science and Practice of Pharmacy, 21st ed., Lippincott Williams & Wilkins, Philadelphia, Pa. (2005).

The opioid antagonists described herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., Journal of Pharmaceutical Sciences, 66:1-19 (1977). The acid addition salts may be obtained as the direct products of compound synthesis. In the alternative, the free base may be dissolved in a suitable solvent containing the appropriate acid and the salt isolated by evaporating the solvent or otherwise separating the salt and solvent. The opioid antagonists described herein may form solvates with standard low molecular weight solvents using methods known to the skilled artisan.

Accordingly, provided herein are pharmaceutical formulations for intranasal administration comprising, in an aqueous solution of not more than about 140 μL:

between about 2 mg and about 12 mg of an opioid antagonist;

between about 0.2 mg and about 1.2 mg of an isotonicity agent;

between about 0.005 mg and about 0.015 mg of a compound which is a preservative, cationic surfactant, and/or permeation enhancer;

between about 0.1 mg and about 0.5 mg of a stabilizing agent;

an amount of an acid sufficient to achieve a pH or 3.5-5.5.

In some embodiments, said opioid antagonist is the only pharmaceutically active compound in said pharmaceutical composition.

In some embodiments, said opioid antagonist is naloxone hydrochloride, or a hydrate thereof.

In some embodiments, said opioid antagonist is naloxone hydrochloride dihydrate.

In some embodiments, the pharmaceutical formulation comprises an amount equivalent to about 4 mg to about 10 mg of naloxone hydrochloride. In some embodiments, the pharmaceutical formulation comprises an amount equivalent to an amount chosen from about 2 mg naloxone hydrochloride, about 4 mg of naloxone hydrochloride, and about 8 mg naloxone hydrochloride. In some embodiments, the pharmaceutical formulation comprises an amount equivalent to about 2 mg of naloxone hydrochloride. In some embodiments, the pharmaceutical formulation comprises an amount equivalent to about 4 mg of naloxone hydrochloride. In some embodiments, the pharmaceutical formulation comprises an amount equivalent to about 8 mg of naloxone hydrochloride. In some embodiments, the therapeutically effective amount is equivalent to about 3.4 mg of naloxone hydrochloride.

In some embodiments, the pharmaceutical formulation comprises about 2.2 mg to about 13.2 mg of naloxone hydrochloride dihydrate. In some embodiments, the pharmaceutical formulation comprises about 4.4 mg to about 11 mg of naloxone hydrochloride dihydrate. In some embodiments, the pharmaceutical formulation comprises an amount chosen from about 2.2 mg naloxone hydrochloride dihydrate, about 4.4 mg of naloxone hydrochloride dihydrate, and about 8.8 mg naloxone hydrochloride dihydrate. In some embodiments, the pharmaceutical formulation comprises about 2.2 mg of naloxone hydrochloride dihydrate. In some embodiments, the pharmaceutical formulation comprises about 4.4 mg of naloxone hydrochloride dihydrate. In some embodiments, the pharmaceutical formulation comprises about 8.8 mg of naloxone hydrochloride dihydrate.

In some embodiments, the device comprises about 4.4 mg naloxone hydrochloride dihydrate. In some embodiments, the device comprises about 2.2 mg naloxone hydrochloride dihydrate.

In some embodiments, the pharmaceutical composition is in an aqueous solution of about 100 μL In some embodiments, upon nasal delivery of said pharmaceutical composition to said patient, less than about 10% of said pharmaceutical composition leaves the nasal cavity via drainage into the nasopharynx or externally.

In some embodiments, the plasma concentration versus time curve of said naloxone hydrochloride in said patient has a $T_{max}$ of between about 20 and about 30 minutes.

In some embodiments, said device is actuatable with one hand.

In some embodiments, the delivery time is less than about 25 seconds. In some embodiments, the delivery time is less than about 20 seconds.

In some embodiments, the 90% confidence interval for dose delivered per actuation is ±about 2%. In some embodiments, the 95% confidence interval for dose delivered per actuation is ±about 2.5%.

In some embodiments, upon nasal delivery of said pharmaceutical composition to said patient, less than about 20% of said pharmaceutical composition leaves the nasal cavity via drainage into the nasopharynx or externally. In some embodiments, upon nasal delivery of said pharmaceutical composition to said patient, less than about 10% of said pharmaceutical composition leaves the nasal cavity via drainage into the nasopharynx or externally. In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in a patient has a $T_{max}$ of less than 30 minutes. In some embodiments, the plasma concentration versus time curve of said opioid antagonist in said patient has a $T_{max}$ of less than 25 minutes. In some embodiments, the plasma concentration versus time curve of said opioid antagonist in said patient has a $T_{max}$ of about 20 minutes. In some embodiments, the plasma concentration versus time curve of the opioid antagonist in the patient has a $T_{max}$ of less than 19 minutes. In some embodiments, the plasma concentration versus time curve of the opioid antagonist in the patient has a $T_{max}$ of about 18.5 minutes.

In some embodiments, delivery of said pharmaceutical formulation to a patient, provides occupancy at $T_{max}$ of said opioid antagonist at the opioid receptors in the respiratory control center of said patient of greater than about 90%. In some embodiments, delivery of said pharmaceutical formulation to said patient, provides occupancy at $T_{max}$ of said opioid antagonist at the opioid receptors in the respiratory control center of said patient of greater than about 95%. In some embodiments, delivery of said pharmaceutical formulation to said patient, provides occupancy at $T_{max}$ of said opioid antagonist at the opioid receptors in the respiratory control center of said patient of greater than about 99%.

In some embodiments, said patient is free from respiratory depression for at least about 1 hour following treatment comprising essentially of delivery of said therapeutically effective amount of said opioid antagonist. In some embodiments, said patient is free from respiratory depression for at least about 2 hours following treatment comprising essentially of delivery of said therapeutically effective amount of said opioid antagonist. In some embodiments, said patient is free from respiratory depression for at least about 4 hours following treatment comprising essentially of delivery of said therapeutically effective amount of said opioid antagonist. In some embodiments, said patient is free from respiratory depression for at least about 6 hours following treatment comprising essentially of delivery of said therapeutically effective amount of said opioid antagonist.

Also provided herein are pharmaceutical formulations for intranasal administration comprising, in an aqueous solution of not more than about 140 µL:
about 2 mg or about 4 mg naloxone hydrochloride or a hydrate thereof;
between about 0.2 mg and about 1.2 mg of an isotonicity agent;
between about 0.005 mg and about 0.015 mg of a compound which is a preservative, cationic surfactant, and/or permeation enhancer;
between about 0.1 mg and about 0.5 mg of a stabilizing agent;
an amount of hydrochloric acid sufficient to achieve a pH or 3.5-5.5.

In some embodiments,
the isotonicity agent is NaCl;
the compound which is a preservative, cationic surfactant, and/or permeation enhancer is benzalkonium chloride;
the stabilizing agent is disodium edetate; and
the acid is hydrochloric acid.

In some embodiments, the pharmaceutical formulation comprises:
about 2.2 mg or about 4.4 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH or 3.5-5.5.

In some embodiments, the pharmaceutical formulation comprises about 4 mg naloxone hydrochloride or a hydrate thereof. In some embodiments, the pharmaceutical formulation comprises about 2 mg naloxone hydrochloride or a hydrate thereof. In some embodiments, the pharmaceutical formulation comprises about 4.4 mg naloxone hydrochloride dihydrate. In some embodiments, the pharmaceutical formulation comprises about 2.2 mg naloxone hydrochloride dihydrate.

Also provided herein are pharmaceutical formulations for intranasal administration comprising, in an aqueous solution of about 100 µL:
about 4 mg naloxone hydrochloride or a hydrate thereof;
between about 0.2 mg and about 1.2 mg of an isotonicity agent;
between about 0.005 mg and about 0.015 mg of a compound which is a preservative, cationic surfactant, and/or permeation enhancer;
between about 0.1 mg and about 0.5 mg of a stabilizing agent;
an amount of an acid sufficient to achieve a pH or 3.5-5.5.

In some embodiments, the pharmaceutical formulation comprises:
about 4.4 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH or 3.5-5.5.

Also provided herein are pharmaceutical formulations for intranasal administration comprising, in an aqueous solution of about 100 µL:
about 2 mg naloxone hydrochloride or a hydrate thereof;
between about 0.2 mg and about 1.2 mg of an isotonicity agent;
between about 0.005 mg and about 0.015 mg of a compound which is a preservative, cationic surfactant, and/or permeation enhancer;

between about 0.1 mg and about 0.5 mg of a stabilizing agent;

an amount of an acid sufficient to achieve a pH or 3.5-5.5.

In some embodiments, the pharmaceutical formulation comprises:

about 2.2 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH or 3.5-5.5.

In some embodiments, the pharmaceutical formulation comprises about 4.4 mg naloxone hydrochloride dihydrate. In some embodiments, the pharmaceutical formulation comprises about 2.2 mg naloxone hydrochloride dihydrate.

Provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 2 mg to about 12 mg of naloxone hydrochloride. In some embodiments, the therapeutically effective amount is equivalent to about 4.4 mg of naloxone hydrochloride. In some embodiments, the therapeutically effective amount is equivalent to about 4.4 mg of naloxone hydrochloride. In some embodiments, the pharmaceutical composition comprises a solution of naloxone hydrochloride dihydrate. In some embodiments, the pharmaceutical composition further comprises one or more excipients selected from water and NaCl. In some embodiments, the pharmaceutical composition is substantially free of antimicrobial preservatives. In some embodiments, the device is substantially free of benzalkonium chloride, methylparaben, sodium benzoate, benzoic acid, phenyl ethyl alcohol In some embodiments, the device is filled with the pharmaceutical composition in a sterile environment. In some embodiments, the pharmaceutical composition is storage-stable for about twelve months at about 25° C. In some embodiments, the pharmaceutical composition comprises less than 0.1% w/w antimicrobial preservatives. In some embodiments, the pharmaceutical composition comprises 0.01% w/w or less antimicrobial preservatives. In some embodiments, the pharmaceutical composition comprises 0.01% w/w-0.001% w/w antimicrobial preservatives. In some embodiments, the pharmaceutical composition comprises less than 0.001% w/w antimicrobial preservatives.

Also provided are devices for "combination-therapy" comprising pharmaceutical compositions comprising at least one opioid antagonist described herein, together with at least one known pharmaceutical agent and a pharmaceutically acceptable carrier. In some embodiments, the pharmaceutical composition comprises a short-acting opioid antagonist and a long-acting opioid antagonist. In some embodiments, the pharmaceutical composition comprises naloxone and naltrexone. In some embodiments, the pharmaceutical composition comprises naloxone and methylnaltrexone. In some embodiments, the pharmaceutical composition comprises naloxone and nalmefene.

Also provided are embodiments wherein any embodiment above may be combined with any one or more of these embodiments, provided the combination is not mutually exclusive.

Indications

Also provided are devices for use in treating opioid overdose and symptoms thereof and methods of using the devices. Naloxone prevents or reverses the effects of opioids including respiratory depression, sedation and hypotension. Also, it can reverse the psychotomimetic and dysphoric effects of agonist-antagonists such as pentazocine. Naloxone causes abrupt reversal of narcotic depression which may result in nausea, vomiting, sweating, tachycardia, increased blood pressure, tremulousness, seizures and cardiac arrest, however, there is no clinical experience with naloxone hydrochloride overdosage in humans. In the mouse and rat the intravenous LD50 is 150±5 mg/kg and 109±4 mg/kg respectively. In acute subcutaneous toxicity studies in newborn rats the LD50 (95% CL) is 260 (228-296) mg/kg. Subcutaneous injection of 100 mg/kg/day in rats for 3 weeks produced only transient salivation and partial ptosis following injection: no toxic effects were seen at 10 mg/kg/day for 3 weeks.

Naloxone hydrochloride injection is indicated for the complete or partial reversal of narcotic depression, including respiratory depression, induced by opioids selected from: natural and synthetic narcotics, propoxyphene, methadone, and certain narcotic-antagonist analgesics: nalbuphine, pentazocine and butorphanol. Naloxone hydrochloride is also indicated for the diagnosis of suspected acute opioid overdosage. For the treatment of known or suspected narcotic overdose in adults an initial dose of 0.4 mg to 2 mg of naloxone hydrochloride intravenously is indicated. If the desired degree of counteraction and improvement in respiratory functions is not obtained, administration may be repeated at 2 to 3 minute intervals. If no response is observed after 10 mg of naloxone hydrochloride have been administered, the diagnosis of narcotic-induced or partial narcotic-induced toxicity should be questioned. The usual initial dose in children is 0.01 mg/kg body weight given IV. If this dose does not result in the desired degree of clinical improvement, a subsequent dose of 0.1 mg/kg body weight may be administered. When using naloxone hydrochloride injection in neonates a product containing 0.02 mg/mL should be used.

It has also been reported that naloxone hydrochloride is an effective agent for the reversal of the cardiovascular and respiratory depression associated with narcotic and possibly some non-narcotic overdoses. The authors stated that due to naloxone's pharmacokinetic profile, a continuous infusion protocol is recommended when prolonged narcotic antagonist effects are required. (Handal et al., Ann Emerg Med. 1983 July; 12(7):438-45).

Accordingly, also provided herein are methods of treating opioid overdose or a symptom thereof, comprising nasally administering to a patient in need thereof a therapeutically effective amount of an opioid antagonist selected from naloxone and pharmaceutically acceptable salts thereof, wherein said therapeutically effective amount is equivalent to about 2 mg to about 12 mg of naloxone hydrochloride or a hydrate thereof. In some embodiments, the therapeutically effective amount of an opioid antagonist selected from naloxone and pharmaceutically acceptable salts thereof is delivered in not more than about 140 μL of an aqueous carrier solution.

In certain embodiments, also provided herein are methods of treating opioid overdose or a symptom thereof, comprising nasally administering to a patient in need thereof a therapeutically effective amount of an opioid antagonist selected from naloxone and pharmaceutically acceptable salts thereof, wherein said therapeutically effective amount is equivalent to about 2 mg to about 12 mg of naloxone hydrochloride or a hydrate thereof in not more than about 140 μL of an aqueous carrier solution.

In certain embodiments, also provided herein are methods of treating opioid overdose or a symptom thereof, comprising nasally administering to a patient in need thereof a single dose of a therapeutically effective amount of an opioid antagonist selected from naloxone and pharmaceutically acceptable salts thereof, wherein said therapeutically effective amount is equivalent to about 2 mg to about 12 mg of naloxone hydrochloride or a hydrate thereof in not more than about 140 µL of an aqueous carrier solution.

In some embodiments, said opioid antagonist is the only pharmaceutically active compound in said pharmaceutical composition.

In some embodiments, said opioid antagonist is naloxone hydrochloride. In some embodiments, said opioid antagonist is naloxone hydrochloride dihydrate.

In some embodiments, said pharmaceutical composition comprises a solution of naloxone hydrochloride, or a hydrate thereof.

In some embodiments, said patient is an opioid overdose patient or a suspected opioid overdose patient.

In some embodiments, said patient is in a lying, supine, or recovery position. In some embodiments, said patient is in a lying position. In some embodiments, said patient is in a supine position. In some embodiments, said patient is in a recovery position.

In some embodiments, said therapeutically effective amount of an opioid antagonist is delivered by an untrained individual.

In some embodiments, said therapeutically effective amount is equivalent to about 4 mg to about 10 mg of naloxone hydrochloride. In some embodiments, said therapeutically effective amount is equivalent to an amount chosen from about 2 mg naloxone hydrochloride, about 4 mg of naloxone hydrochloride, and about 8 mg naloxone hydrochloride. In some embodiments, said therapeutically effective amount is equivalent to about 2 mg of naloxone hydrochloride. In some embodiments, said therapeutically effective amount is equivalent to about 4 mg of naloxone hydrochloride. In some embodiments, said therapeutically effective amount is equivalent to about 8 mg of naloxone hydrochloride. In some embodiments, the therapeutically effective amount is equivalent to about 3.4 mg of naloxone hydrochloride.

In some embodiments, said therapeutically effective amount is about 2.2 mg to about 13.2 mg of naloxone hydrochloride dihydrate. In some embodiments, said therapeutically effective amount is about 4.4 mg to about 11 mg of naloxone hydrochloride dihydrate. In some embodiments, said therapeutically effective amount is an amount chosen from about 2.2 mg naloxone hydrochloride dihydrate, about 4.4 mg of naloxone hydrochloride dihydrate, and about 8.8 mg naloxone hydrochloride dihydrate. In some embodiments, said therapeutically effective amount is about 2.2 mg of naloxone hydrochloride dihydrate. In some embodiments, said therapeutically effective amount is about 4.4 mg of naloxone hydrochloride dihydrate. In some embodiments, said therapeutically effective amount is about 8.8 mg of naloxone hydrochloride dihydrate.

In some embodiments, said symptom is chosen from respiratory depression and central nervous system depression.

In some embodiments, said patient exhibits any of unresponsiveness to stimulus, unconsciousness, stopped breathing; erratic or stopped pulse, choking or gurgling sounds, blue or purple fingernails or lips, slack or limp muscle tone, contracted pupils, and vomiting.

In some embodiments, said patient is not breathing.

In some embodiments, said patient is in a lying, supine, or recovery position.

In some embodiments, said patient is in a lying position.

In some embodiments, said patient is in a supine position.

In some embodiments, said patient is a recovery position.

In some embodiments, said therapeutically effective amount is equivalent to about 2 mg to about 10 mg of naloxone hydrochloride.

In some embodiments, said therapeutically effective amount is equivalent to an amount chosen from about 2 mg naloxone hydrochloride, about 4 mg of naloxone hydrochloride, and about 8 mg naloxone hydrochloride.

In some embodiments, said therapeutically effective amount is equivalent to about 2 mg of naloxone hydrochloride.

In some embodiments, said therapeutically effective amount is equivalent to about 4 mg of naloxone hydrochloride.

In some embodiments, said therapeutically effective amount is equivalent to about 8 mg of naloxone hydrochloride.

In some embodiments, said opioid antagonist is the only pharmaceutically active compound in said pharmaceutical composition.

In some embodiments, said opioid antagonist is naloxone hydrochloride.

In some embodiments, said nasally administering is accomplished using a pre-primed device adapted for nasal delivery of a pharmaceutical composition.

In some embodiments, upon nasal delivery of said pharmaceutical composition to said patient, less than about 20% of said pharmaceutical composition leaves the nasal cavity via drainage into the nasopharynx or externally.

In some embodiments, upon nasal delivery of said pharmaceutical composition to said patient, less than about 10% of said pharmaceutical composition leaves the nasal cavity via drainage into the nasopharynx or externally.

In some embodiments, upon nasal delivery of said pharmaceutical composition to said patient, less than about 5% of said pharmaceutical composition leaves the nasal cavity via drainage into the nasopharynx or externally.

In some embodiments, the plasma concentration versus time curve of said opioid antagonist in said patient has a $T_{max}$ of less than 30 minutes.

In some embodiments, the plasma concentration versus time curve of said opioid antagonist in said patient has a $T_{max}$ of less than 25 minutes.

In some embodiments, the plasma concentration versus time curve of said opioid antagonist in said patient has a $T_{max}$ of about 20 minutes.

In some embodiments, said opioid overdose symptom is selected from: respiratory depression, central nervous system depression, and cardiovascular depression.

In some embodiments, said opioid overdose symptom is respiratory depression induced by opioids.

In some embodiments, said respiratory depression is caused by the illicit use of opioids or by an accidental misuse of opioids during medical opioid therapy.

In some embodiments, said respiratory depression is induced by opioids selected from: natural and synthetic narcotics, propoxyphene, methadone, nalbuphine, pentazocine and butorphanol.

In some embodiments, said respiratory depression is induced by an opioid selected from codeine, morphine, methadone, fentanyl, oxycodone HCl, hydrocodone bitartrate, hydromorphone, oxymorphone, meperidine, propoxyphene, opium, heroin, tramadol, tapentadol.

In some embodiments, said patient is free from respiratory depression for at least about 1 hour following treatment comprising essentially of delivery of said therapeutically effective amount of said opioid antagonist.

In some embodiments, said patient is free from respiratory depression for at least about 2 hours following treatment comprising essentially of delivery of said therapeutically effective amount of said opioid antagonist.

In some embodiments, said patient is free from respiratory depression for at least about 4 hours following treatment comprising essentially of delivery of said therapeutically effective amount of said opioid antagonist.

In some embodiments, said patient is free from respiratory depression for at least about 6 hours following treatment comprising essentially of delivery of said therapeutically effective amount of said opioid antagonist.

Also provided are embodiments wherein any embodiment above may be combined with any one or more of these embodiments, provided the combination is not mutually exclusive.

Also provided are the devices, pharmaceutical compositions, kits, and methods of treatment described herein for use in the treatment of an opioid overdose symptom selected from: respiratory depression, postoperative opioid respiratory depression, altered level consciousness, miotic pupils, cardiovascular depression, hypoxemia, acute lung injury, aspiration pneumonia, sedation, and hypotension. Also provided are the devices, pharmaceutical compositions, kits, and methods of treatment described herein for use in the reversal of respiratory depression induced by opioids. In some embodiments, the respiratory depression is caused by the illicit use of opioids or by an accidental misuse of opioids during medical opioid therapy. Also provided are the devices, pharmaceutical compositions, kits, and methods of treatment described herein for use in the complete or partial reversal of narcotic depression, including respiratory depression, induced by opioids selected from: natural and synthetic narcotics, propoxyphene, methadone, nalbuphine, pentazocine and butorphanol. In some embodiments, narcotic depression, including respiratory depression, is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Also provided are devices, pharmaceutical formulations, and kits for, and methods of, treating opioid overdose or a symptom thereof, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the patient is not breathing. Also provided are devices adapted for nasal delivery of a pharmaceutical composition to a patient, comprising a therapeutically effective amount of an opioid antagonist selected from naloxone and pharmaceutically acceptable salts thereof, wherein the device is pre-primed, and wherein the therapeutically effective amount, is equivalent to about 4 mg to about 12 mg of naloxone hydrochloride. In some embodiments, the therapeutically effective amount is equivalent to about 2 mg to about 24 mg of naloxone hydrochloride. In some embodiments, the therapeutically effective amount is equivalent to about 3 mg to about 18 mg of naloxone hydrochloride. In some embodiments, the therapeutically effective amount is equivalent to about 4 mg to about 10 mg of naloxone hydrochloride. In some embodiments, the therapeutically effective amount is equivalent to about 5 mg to about 11 mg of naloxone hydrochloride. In some embodiments, the therapeutically effective amount is equivalent to about 6 mg to about 10 mg of naloxone hydrochloride. In some embodiments, the therapeutically effective amount is equivalent to about 4 mg to about 8 mg of naloxone hydrochloride. In some embodiments, the therapeutically effective amount is equivalent to about 7 mg to about 9 mg of naloxone hydrochloride. In some embodiments, the therapeutically effective amount is equivalent to about 3.4 mg of naloxone hydrochloride. In some embodiments, the therapeutically effective amount is equivalent to about 4 mg of naloxone hydrochloride. In some embodiments, the therapeutically effective amount is equivalent to about 5 mg of naloxone hydrochloride. In some embodiments, the therapeutically effective amount is equivalent to about 6 mg of naloxone hydrochloride. In some embodiments, the therapeutically effective amount is equivalent to about 7 mg of naloxone hydrochloride. In some embodiments, the therapeutically effective amount is equivalent to about 8 mg of naloxone hydrochloride. In some embodiments, the therapeutically effective amount is equivalent to about 9 mg of naloxone hydrochloride. In some embodiments, the therapeutically effective amount is equivalent to about 10 mg of naloxone hydrochloride. In some embodiments, the therapeutically effective amount is equivalent to about 11 mg of naloxone hydrochloride. In some embodiments, the therapeutically effective amount is equivalent to about 12 mg of naloxone hydrochloride. In some embodiments, the opioid antagonist is the only pharmaceutically active compound in pharmaceutical composition. In some embodiments, the opioid antagonist is naloxone hydrochloride. In some embodiments, the opioid antagonist is anhydrous naloxone hydrochloride. In some embodiments, the opioid antagonist is the only pharmaceutically active compound in said pharmaceutical composition. In some embodiments, the opioid antagonist is naloxone hydrochloride. In some embodiments, the pharmaceutical composition comprises a solution of naloxone hydrochloride. In some embodiments, the nasally administering is accomplished using a device described herein. In some embodiments, the opioid overdose symptom is selected from: respiratory depression, postoperative opioid respiratory depression, altered level consciousness, miotic pupils, cardiovascular depression, hypoxemia, acute lung injury, aspiration pneumonia, sedation, and hypotension. In some embodiments, the opioid overdose symptom is respiratory depression induced by opioids. In some embodiments, the respiratory depression is caused by the illicit use of opioids or by an accidental misuse of opioids during medical opioid therapy. In some embodiments, the respiratory depression is induced by opioids selected from: natural and synthetic narcotics, propoxyphene, methadone, nalbuphine, pentazocine and butorphanol. In some embodiments, the respiratory depression is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Also provided are devices, kits, and pharmaceutical formulations for, and methods of, treating opioid overdose or a symptom thereof, comprising nasally administering to a patient in need thereof a therapeutically effective amount of an opioid antagonist together and at least one known pharmaceutical agent. In some embodiments, the method comprises nasally administering to a patient in need thereof therapeutically effective amounts of a short-acting opioid antagonist and a long-acting opioid antagonist. In some embodiments, the method comprises nasally administering to a patient in need thereof therapeutically effective amounts of naloxone and naltrexone. In some embodiments, the method comprises nasally administering to a patient in need thereof therapeutically effective amounts of naloxone and methylnaltrexone. In some embodiments, the method comprises nasally administering to a patient in need thereof therapeutically effective amounts of naloxone and nalmefene.

Also provided are devices, kits, and pharmaceutical formulations for, and methods of, reversing the psychotomimetic and dysphoric effects of agonist-antagonists such as pentazocine, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4.4 mg of naloxone hydrochloride. In some embodiments, the therapeutically effective amount is equivalent to about 4 mg of naloxone hydrochloride dihydrate. In some embodiments, the nasally administering is accomplished using a device described herein.

Also provided are devices, kits, and pharmaceutical formulations for, and methods of, diagnosis of suspected acute opioid overdosage, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4 mg of naloxone hydrochloride. In some embodiments, the therapeutically effective amount is equivalent to about 4.4 mg of naloxone hydrochloride dihydrate. In some embodiments, the nasally administering is accomplished using a device described herein.

Also provided are devices, kits, and pharmaceutical formulations for, and methods of, treating opioid addiction, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4 mg of naloxone hydrochloride. In some embodiments, the therapeutically effective amount is equivalent to about 4.4 mg of naloxone hydrochloride dihydrate. In some embodiments, the nasally administering is accomplished using a device described herein.

Also provided are devices, kits, and pharmaceutical formulations for, and methods of, treating septic shock, comprising nasally administering to a patient in need thereof a therapeutically effective amount of an opioid antagonist selected from naloxone and pharmaceutically acceptable salts thereof, wherein the therapeutically effective amount is equivalent to about 2 mg to about 12 mg of naloxone hydrochloride. In some embodiments, the therapeutically effective amount is equivalent to about 4 mg of naloxone hydrochloride. In some embodiments, the therapeutically effective amount is equivalent to about 4.4 mg of naloxone hydrochloride dihydrate. In some embodiments, the nasally administering is accomplished using a device described herein.

Also provided are devices, kits, and pharmaceutical formulations for, and methods of, treating opioid overdose or a symptom thereof, reversing the psychotomimetic and dysphoric effects of agonist-antagonists such as pentazocine, diagnosing suspected acute opioid overdosage, treating opioid addiction, or treating septic shock, comprising nasally administering to a patient in need thereof a therapeutically effective amount of an opioid antagonist, wherein the therapeutically effective amount is about 2 mg to about 12 mg. In some embodiments, the therapeutically effective amount is equivalent to about 4.4 mg of naloxone hydrochloride dihydrate. In some embodiments, the therapeutically effective amount is equivalent to about 4 mg of naloxone hydrochloride. In some embodiments, the patient is an opioid overdose patient. In some embodiments, the patient is not breathing. In some embodiments, the opioid antagonist is the only pharmaceutically active compound in said pharmaceutical composition. In some embodiments, the opioid antagonist is selected from naltrexone, methylnaltrexone, and nalmefene, and pharmaceutically acceptable salts thereof. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the nasally administering is accomplished using a device described herein. In some embodiments, the opioid overdose symptom is selected from: respiratory depression, postoperative opioid respiratory depression, altered level consciousness, miotic pupils, cardiovascular depression, hypoxemia, acute lung injury, aspiration pneumonia, sedation, and hypotension. In some embodiments, the opioid overdose symptom is respiratory depression induced by opioids. In some embodiments, the respiratory depression is caused by the illicit use of opioids or by an accidental misuse of opioids during medical opioid therapy. In some embodiments, the respiratory depression is induced by opioids selected from: natural and synthetic narcotics, propoxyphene, methadone, nalbuphine, pentazocine and butorphanol. In some embodiments, the respiratory depression is induced by an opioid agonist selected from codeine, morphine, methadone, fentanyl, oxycodone HCl, hydrocodone bitartrate, hydromorphone, oxymorphone, meperidine, propoxyphene, opium, heroin, tramadol, and tapentadol.

Various eating disorders, including binge eating, bulimia, and stimulus-induced over-eating, develop because the behaviors are reinforced by the opioidergic system so often and so well that the person no longer can control the behavior. Thus eating disorders resemble opiate addiction and alcoholism. Accordingly, also provided are devices, kits, and pharmaceutical formulations for, and methods of, treating an eating disorder selected from binge eating, bulimia, and stimulus-induced over-eating, comprising nasally administering to a patient in need thereof a therapeutically effective amount of an opioid antagonist, wherein the therapeutically effective amount is about 2 mg to about 12 mg. In some embodiments, the therapeutically effective amount is equivalent to about 4 mg of naloxone hydrochloride. In some embodiments, the therapeutically effective amount is equivalent to about 4.4 mg of naloxone hydrochloride. In some embodiments, the opioid antagonist is the only pharmaceutically active compound in said pharmaceutical composition. In some embodiments, the opioid antagonist is selected from naltrexone, methylnaltrexone, and nalmefene, and pharmaceutically acceptable salts thereof. In some embodiments, the opioid antagonist is naltrexone hydrochloride. In some embodiments, the opioid antagonist is methylnaltrexone bromide. In some embodiments, the opioid antagonist is nalmefene hydrochloride. In some embodiments, the nasally administering is accomplished using a device described herein.

Also provided are embodiments wherein any embodiment above may be combined with any one or more of these embodiments, provided the combination is not mutually exclusive.

Receptor Occupancy

Also provided are devices for use in treating opioid overdose and symptoms thereof and methods of using the devices, which provide a high level of brain opioid receptor occupancy as may be determined, for example, by positron emission tomography (PET). PET and single-photon emission computed tomography (SPECT) are noninvasive imaging techniques that can give insight into the relationship between target occupancy and drug efficacy, provided a suitable radioligand is available. Although SPECT has certain advantages (e.g., a long half-life of the radionuclides), the spatial and temporal resolution as well as the labeling possibilities of this technique are limited.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides. Positron-emitting radionuclides include 11C, $^{13}$N, $^{15}$O, $^{18}$F, $^{52}$Fe, $^{62}$Cu, $^{64}$Cu, $^{68}$Ga, $^{74}$As, $^{82}$Rb, $^{89}$Zr, $^{122}$I, and $^{124}$I. Non-metal radionuclides may be covalently linked to the targeting molecule by reactions well known from the state of art. When the radionuclide is a metallic positron-emitter, it is understood that labeling may require the use of a chelating agent. Such chelating agents are well known from the state of the art.

The positron-emitter labeled compound is administered directly, e.g., IV, or indirectly, e.g., IN, into the subject's vascular system, from where it passes through the blood-brain barrier. Once the tracer has had sufficient time to associate with the target of interest, the individual is placed within in a scanning device comprising ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored. An image is then generated of the part of the individual's brain to which the compound has distributed.

PET studies are useful for comparing nasal delivery of naloxone using the devices and at the doses described herein, to typical nasal doses of naloxone (such as 1-2 mg), to delivery of naloxone using other nasal devices (such as the MAD™) and by other routes of administration such IM or IV naloxone or oral naltrexone or nalmefene. Further comparisons may be made between nasal administration in the upright versus the lying or supine positions. Useful measures that may be determined in such studies are the time to onset of action, brain half-life, and the percent receptor binding or occupancy of a patient's opioid receptors, for example, the μ-opioid receptors in the respiratory center in the medulla oblongata.

[$^{11}$C]Carfentanil (CFN) is a μ-opioid agonist used for in vivo PET studies of μ-opioid receptors. One such study involved healthy male volunteers assigned at enrolment to receive either naltrexone or a novel μ-opioid receptor inverse agonist (GSK1521498) (Rabiner et al., *Pharmacological differentiation of opioid receptor antagonists by molecular and functional imaging of target occupancy and food reward-related brain activation in humans*. Molecular Psychiatry (2011) 16, 826-835). Each participant underwent up to three [$^{11}$C]-carfentanil PET scans and two fMRI examinations: one [$^{11}$C]-carfentanil PET scan and one fMRI scan at baseline (before dosing) and up to two PET scans and one fMRI scan following oral administration of a single dose of GSK1521498 or naltrexone. The administered doses of GSK1521498 or naltrexone were chosen adaptively to optimize the estimation of the dose-occupancy relationship for each drug on the basis of data acquired from the preceding examinations in the study. The administered dose range was 0.4-100 mg for GSK1521498, and 2-50 mg for naltrexone. The maximum doses administered were equal to the maximum tolerated dose of GSK1521498 determined in the first-in-human study and the standard clinical dose of naltrexone used for alcohol dependence. The times and doses of the two post-dose [$^{11}$C]-carfentanil PET scans were chosen adaptively for each subject to optimize estimation of the relationship between plasma concentration and receptor occupancy. Post-dose [$^{11}$C]-carfentanil PET scans were acquired at 3-36 h after the administration of GSK1521498 and at 3-88 h after the administration of naltrexone. Post-dose fMRI scans were acquired within 60 min of the first post-dose PET scan. Venous blood samples were collected at regular intervals throughout the scanning sessions. High-performance liquid chromatography/mass spectrometry/mass spectrometry was used to estimate the plasma concentrations of GSK1521498, naltrexone, and the major metabolite of naltrexone, 6-β-naltrexol. Drug plasma concentration at the start of each PET scan was used to model the relationship between drug concentrations and μ-opioid receptor occupancies. Carfentanil (methyl 1-(2-phenyl-ethyl)-4-(phenyl(propanoyl)amino)-4-piperidinecarboxylate 3S, 5S; Advanced Biochemical Compounds, Radeberg, Germany), a potent selective μ-opioid receptor agonist, was labelled with carbon-11 using a modification of a previously described method implemented using a semiautomated Modular Lab Multifunctional Synthetic Module (Eckert & Ziegler, Berlin, Germany). The final product was reformulated in sterile 0.9% saline containing ~10% ethanol (v/v) and satisfied quality control criteria for specific activity and purity before being injected intravenously as a slow bolus over ~30 s. PET scanning was conducted in three-dimensional mode using a Siemens Biograph 6 Hi-Rez PET-CT for the naltrexone group and a Siemens Biograph 6 TruePoint PET-CT for the GSK1521498 group (Siemens Healthcare, Erlangen, Germany). A low-dose CT scan was acquired for attenuation correction before the administration of the radiotracer. Dynamic PET data were acquired for 90 min after [$^{11}$C]-carfentanil injection, binned into 26 frames (durations: 8×15 s, 3×60 s, 5×2 min, 5×5 min and 5×10 min), reconstructed using Fourier re-binning and a two-dimensional-filtered back projection algorithm and then smoothed with a two-dimensional Gaussian filter (5 mm at full width half maximum). Dynamic PET images were registered to each participant's T1-weighted anatomical MRI volume and corrected for head motion using SPM5 software (Wellcome Trust Centre for Neuroimaging). Pre-selected regions of interests were defined bilaterally on the T1-weighted anatomical volume using an in-house atlas and applied to the dynamic PET data to generate regional time-activity curves. The [$^{11}$C]-carfentanil-specific binding was quantified as binding potential relative to the non-displaceable compartment ($BP_{ND}$)

$$BP_{ND} = \frac{f_{ND} B_{avail}}{K_D}$$

where fND is the free fraction of the radioligand in the brain, $K_D$ is the affinity of [$^{11}$C]-carfentanil, and $B_{avail}$ is the density of the available μ-opioid receptors. Regional [$^{11}$C]-carfentanil $BP_{ND}$ was estimated using a reference tissue model with the occipital cortex as the reference region. Drug related occupancy of the μ-opioid receptor was quantified as a reduction of [$^{11}$C]-carfentanil.

$$Occupancy_{Drug} = \frac{BP_{ND}^{Baseline} - BP_{ND}^{Drug}}{BP_{ND}^{Baseline}}$$

The affinity constant for each drug at the μ-opioid receptor (effective concentration 50 ($EC_{50}$)) was estimated by fitting the plasma concentration measured at the start of the PET scan, $C^P_{Drug}$, to the estimated occupancy:

$$Occupancy_{Drug} = \frac{C^P_{Drug}}{C^P_{Drug} + EC_{50}}$$

The use of a sensitive non-tomographic positron detecting system to measure the dose-response curve of naloxone in human brain has also been reported. [$^{11}$C]Diprenorphine was administered to normal volunteers in tracer amounts and, 30 min later, various bolus doses of naloxone were given (1.5-160 μg/kg) intravenously and change in [$^{11}$C] diprenorphine binding monitored over the next 30 min. Approximately 13 μg/kg of naloxone (approximately 1 mg in an 80 kg man) was required to produce an estimated 50% receptor occupation, consistent with the clinical dose of naloxone used to reverse opiate overdose (0.4 mg-1.2 mg). Melichar et al., *Naloxone displacement at opioid receptor sites measured in vivo in the human brain*. Eur J Pharmacol. 2003 Jan. 17; 459(2-3):217-9).

In some embodiments of the devices, kits, pharmaceutical formulations, and methods disclosed above, delivery of the therapeutically effective amount to the patient, provides occupancy at $T_{max}$ of the opioid antagonist at the opioid receptors in the respiratory control center of the patient of greater than about 90%. In some embodiments, delivery of the therapeutically effective amount to the patient, provides occupancy at $T_{max}$ of the opioid antagonist at the opioid receptors in the respiratory control center of the patient of greater than about 95%. In some embodiments, delivery of the therapeutically effective amount to the patient, provides occupancy at $T_{max}$ of the opioid antagonist at the opioid receptors in the respiratory control center of the patient of greater than about 99%. In some embodiments, delivery of the therapeutically effective amount to the patient, provides occupancy at $T_{max}$ of the opioid antagonist at the opioid receptors in the respiratory control center of the patient of about 100%.

Also provided are embodiments wherein any embodiment described above, may be combined with any one or more of these embodiments, provided the combination is not mutually exclusive.

EXAMPLES

Example 1

Pharmacokinetics and Safety of Intranasal Naloxone in Humans (Study 1)

A clinical trial was performed for which the primary objectives were to determine the pharmacokinetics (PK) of 2 intranasal (IN) doses (2 mg and 4 mg) of naloxone compared to a 0.4 mg dose of naloxone administrated intramuscularly (IM) and to identify an appropriate IN dose that could achieve systemic exposure comparable to an approved parenteral dose. The secondary objectives were to determine the safety of IN naloxone, specifically with respect to nasal irritation (erythema, edema, and erosion).

Methodology: This was an inpatient open-label, randomized, 3-period, 3-treatment, 6-sequence, crossover study involving 14 healthy volunteers. Subjects were assigned to one of the 6 sequences with 2 subjects in each sequence (2 sequences had 3 subjects). Each subject received 3 naloxone doses, a single 2 mg IN dose (one spray of 0.1 mL of 10 mg/mL solution in each nostril), a single 4 mg IN dose (2 sprays of 0.1 mL per spray of 10 mg/mL solution in each nostril) and a single 0.4 mg IM dose, in the 3 dosing periods (Table 1). Subjects stayed in the inpatient facility for 11 days to complete the entire study and were discharged on the next day after the last dose. Subjects returned for a final follow-up visit 3-5 days after discharge. After obtaining informed consent, subjects were screened for eligibility to participate in the study including medical history, physical examination, clinical chemistry, coagulation markers, hematology, infectious disease serology, urinalysis, urine drug and alcohol toxicology screen, vital signs and electrocardiogram (ECG). On the day after clinic admission, subjects were administered study drug in randomized order with a 4-day washout period between doses until all three doses were administered. Blood was collected for naloxone PK prior to dosing and approximately 2.5, 5, 10, 15, 20, 30, 45, 60, 120, 180, 240, 300, 360, 480 and 720 min after the start of study drug administration. On days of study drug administration, a 12-lead ECG was performed approximately 60 min prior to dosing and at approximately 60 and 480 min post-dose. Vital signs were measured pre-dose and approximately 30, 60, 120, and 480 min post-dose. On dosing days, the order of assessments was ECG, vital signs, then PK blood collection when scheduled at the same nominal times. ECG and vital signs were collected within the 10-min period before the nominal time of blood collections. At screening, admission, discharge, and follow-up, ECG and vital signs were checked once per day. Vital signs were also checked once on the day after naloxone administration. Clinical laboratory measurements were repeated after the last PK blood draw prior to clinic discharge. AEs were assessed by spontaneous reports by subjects, examination of the nasal mucosa, physical examination, vital signs, ECG, and clinical laboratory parameters.

Main Criteria for Inclusion/Exclusion: Healthy volunteer adults with a body mass index (BMI) of 18-30 kg/m$^2$.

Investigational Product, Dose and Mode of Administration: Naloxone given IN was at a dose of 2 mg (1 squirt in each nostril delivered 0.1 mL of 10 mg/mL naloxone) and 4 mg (2 squirts in each nostril delivered 0.2 mL/nostril at 10 mg/mL naloxone, using two devices). IN naloxone was administered using a Pfeiffer (Aptar) BiDose liquid device with the subject in a fully supine position.

Duration of Treatment: Each IN and IM dose was administered once in each subject in random sequence.

Reference Therapy, Dose and Mode of Administration: Naloxone was given IM at a dose of 0.4 mg in 1.0 mL with a 23-g needle as a single injection in the gluteus maximus muscle.

PK Evaluation: Blood was collected in sodium heparin containing tubes for naloxone PK prior to dosing and 2.5, 5, 10, 15, 20, 30, 45, 60, 120, 180, 240, 300, 360, 480, and 720 min after the start of study drug administration. Non-compartmental PK parameters including $C_{max}$, $T_{max}$, AUC to infinity ($AUC_{0-\infty}$), AUC to last measurable concentration ($AUC_{0-t}$), $t_{1/2}$, $\lambda_z$, and apparent clearance (CL/F) were determined. Values of $t_{1/2}$ were determined from the log-linear decline in plasma concentrations from 2 to 6 or 8 h.

Safety Evaluation: Heart rate, blood pressure, and respiration rate was recorded before naloxone dosing and at approximately 30, 60, 120, and 480 min after dosing. These vital signs and temperature were also measured at screening, clinic intake, one day after each dosing session and at follow-up. A 12-lead ECG was obtained prior to and approximately 60 and 480 min after each naloxone dose, as well as during screening, clinic intake, and follow-up. ECG and vital signs were taken within the 10-min period before the nominal time for blood collections. AEs were recorded from the start of study-drug administration until clinic discharge. AEs were recorded relative to each dosing session to attempt to establish a relationship between the AE and type of naloxone dose administered. An examination of the nasal passage was conducted at Day-1 to establish eligibility and at pre-dose, 5 min, 30 min, 60 min, 4 h, and 24 h post naloxone administration to evaluate evidence of irritation to the nasal mucosa. Clinical laboratory measurements were done prior to the first drug administration and on the day of clinic release.

Statistical Analysis of PK Parameters: $C_{max}$, $T_{max}$ and AUC for 2 and 4 mg IN naloxone were compared with those for 0.4 mg IM naloxone. Within an ANOVA framework, comparisons of natural log (LN) transformed PK parameters ($C_{max}$ and AUC) for IN versus IM naloxone treatments were performed. The 90% confidence interval (CI) for the ratio (IN/IM) of the least squares means of AUC and $C_{max}$ parameters was constructed. These 90% CI were obtained by exponentiation of the 90% confidence intervals for the difference between the least squares means based upon a LN scale. In addition, dose adjusted values for AUCs and $C_{max}$ based upon a 0.4 mg dose were calculated (Tables 4-7). The relative extent of absorption (relative bioavailability, $F_{rel}$) of intranasal (IN versus IM) was estimated from the dose-corrected AUCs.

Statistical Analysis of Adverse Events: AEs were coded using the most recent version of the Medical Dictionary for Regulatory Activities (MedDRA). Preferred terms and are grouped by system, organ, class (SOC) designation. AEs are presented as a listing including the start date, stop date, severity, relationship, outcome, and duration.

Pharmacokinetics Results: The mean dose delivered for the 2 mg IN naloxone dose was 1.71 mg (range 1.50 mg to 1.80 mg) and for the 4 mg IN naloxone dose it was 3.40 mg (range 2.93 mg to 3.65 mg). This was 84-85% of the target dose. The overall % coefficient of variation (% CV) for the delivered dose from all 42 devices was 6.9% (Table 9). Preparation time of the IN doses took less than one third of the time to prepare the IM injection (70 seconds for the IM injection and 20 seconds for the IN administration) (Table 8). The time to prepare the IM injection did not include loading the syringe. Since the one purpose of the study was to determine if peak naloxone plasma concentrations ($C_{max}$) and AUCs following IN 2 mg and IN 4 mg administrations were equivalent to, or greater than IM 0.4 mg dosing, AUCs and $C_{max}$ values were compared without considering the dose difference among treatments. The $C_{max}$, $AUC_{0-t}$, and $AUC_{0-\infty}$ for both the 2 mg IN and 4 mg IN doses were statistically significantly greater than those for the 0.4 mg IM dose (p<0.001). The geometric least square means for $C_{max}$ were 2.18 ng/mL, 3.96 ng/mL, and 0.754 ng/mL for IN 2 mg, IN 4 mg and IM 0.4 mg, respectively. The geometric least square means for $AUC_{0-\infty}$ were 3.32 ng·h/mL, 5.47 ng·h/mL and 1.39 ng·h/mL for IN 2 mg, IN 4 mg and IM 0.4 mg respectively. The geometric least squares mean ratios for IN 2 mg/IM 0.4 mg were 290% for $C_{max}$ and 239% for $AUC_{0-\infty}$. The ratios for IN 4 mg/IM 0.4 mg were 525% for $C_{max}$ and 394% for $AUC_{0-\infty}$. There were no statistically significant differences between the routes and doses with respect to $T_{max}$, suggesting peak effects would occur at similar times for all treatments. However, the mean $T_{max}$ values did trend lower for the IN route versus IM, and for 4 mg IN versus 2 mg IN. (See Table 2). In comparing the extent of systemic absorption of IN to IM dosing, the $F_{rel}$ estimates were 55.7% and 46.3% for IN 2 mg and 4 mg, respectively. See Table 3.

Safety Results: No erythema, edema, erosion, or other sign was observed in the nasal cavity prior to or after any IN administration of naloxone at 2 and 4 mg to both nostrils. One subject experienced mild transient (over 3 min) pharyngeal pain coincident with the application of the 2 mg IN dose. This pain resolved spontaneously. Vital signs, ECG, and clinical laboratory parameters did not reveal any clinically noteworthy changes after naloxone administration. There was no evidence of QTcF prolongation.

TABLE 1

Order of Naloxone Doses and Route of Administration for each Subject

| # | Subject ID | Sequence # | Dosing Session #1 Day 1 | Dosing Session #2 Day 5 | Dosing Session #3 Day 9 |
|---|---|---|---|---|---|
| 1 | 102 | 5 | 4 mg IN | 2 mg IN | 0.4 mg IM |
| 2 | 107 | 6 | 0.4 mg IM | 4 mg IN | 2 mg IN |
| 3 | 112 | 1 | 2 mg IN | 4 mg IN | 0.4 mg IM |
| 4 | 117 | 3 | 0.4 mg IM | 2 mg IN | 4 mg IN |
| 5 | 120 | 1 | 2 mg IN | 4 mg IN | 0.4 mg IM |
| 6 | 123 | 2 | 4 mg IN | 0.4 mg IM | 2 mg IN |
| 7 | 127 | 3 | 0.4 mg IM | 2 mg IN | 4 mg IN |
| 8 | 128 | 5 | 4 mg IN | 2 mg IN | 0.4 mg IM |
| 9 | 133 | 2 | 4 mg IN | 0.4 mg IM | 2 mg IN |
| 10 | 113 | 4 | 2 mg IN | 0.4 mg IM | 4 mg IN |
| 11 | 114 | 1 | 2 mg IN | 4 mg IN | 0.4 mg IM |
| 12 | 119 | 6 | 0.4 mg IM | 4 mg IN | 2 mg IN |
| 13 | 125 | 4 | 2 mg IN | 0.4 mg IM | 4 mg IN |
| 14 | 135 | 5 | 4 mg IN | 2 mg IN | 0.4 mg IM |

TABLE 2

Summary of Naloxone Pharmacokinetic Parameters Following Naloxone as 0.4 mg Intramuscular (IM), 2 mg Intranasal (IN), and 4 mg IN Administrations

| Parameter | 0.4 mg IM | | 2 mg IN | | 4 mg IN | |
|---|---|---|---|---|---|---|
| | Mean | % CV | Mean | % CV | Mean | % CV |
| Dose (mg) | 0.400 | — | 1.714 | 5.7 | 3.403 | 5.7 |
| $C_{max}$ (ng/mL) | 0.765 | 27.6 | 2.32 | 41.2 | 4.55 | 63.7 |
| $T_{max}$ (min) | 20.34 | 36.1 | 19.98 | 31.0 | 18.42 | 33.6 |

TABLE 2-continued

Summary of Naloxone Pharmacokinetic Parameters Following Naloxone as 0.4 mg Intramuscular (IM), 2 mg Intranasal (IN), and 4 mg IN Administrations

| Parameter | 0.4 mg IM Mean | % CV | 2 mg IN Mean | % CV | 4 mg IN Mean | % CV |
|---|---|---|---|---|---|---|
| $AUC_{0-t}$ ng · h/mL | 1.38 | 19.9 | 3.41 | 29.5 | 5.63 | 27.6 |
| $AUC_{0-\infty}$ (ng · h/mL) | 1.42 | 19.2 | 3.44 | 29.3 | 5.68 | 27.6 |
| $\lambda_z$ (1/h) | 0.593 | 16.6 | 0.588 | 0.572 | 8.0 | 10.2 |
| $t_{1/2}$ (h) | 1.21 | 20.1 | 1.19 | 8.3 | 1.22 | 10.2 |

TABLE 3

Summary of Naloxone Pharmacokinetic Parameters Following Naloxone as 0.4 mg Intramuscular (IM), 2 mg Intranasal (IN), and 4 mg IN Administrations with Dose Normalized to 0.4 mg

| Parameter | 0.4 mg IM Mean | % CV | 2 mg IN Mean | % CV | 4 mg IN Mean | % CV |
|---|---|---|---|---|---|---|
| $AUC_{0-t/D}$ ng · h/mL | 1.38 | 19.9 | 0.796 | 28.7 | 0.667 | 29.4 |
| $AUC_{0-\infty/D}$ ng · h/mL | 1.42 | 19.2 | 28.5 | 0.674 | 0.804 | 29.3 |
| $F_{rel}$ | | | 0.571 | 24.5 | 0.475 | 25.3 |

TABLE 4

Statistical Comparison of Geometric Least Squares Mean (GLSM) of Pharmacokinetic Parameters for IN Naloxone at a Dose of 2 mg to IM Naloxone at a Dose of 0.4 mg with No Dose Adjustment

| Parameter | GLSM 2 mg IN | GLSM 0.4 mg IM | GLSM Ratio IM/IN % | 90% CI of Ratio | p-value |
|---|---|---|---|---|---|
| $C_{max}$ (ng/mL) | 2.18 | 0.754 | 290 | 237-353 | <0.001 |
| $T_{max}$ (h) | 1.000 | 0.333 | 0.308 | — | — | — |
| $AUC_{0-t}$ (ng · h/mL) | 3.28 | 1.35 | 243 | 219-270 | <0.001 |
| $AUC_{0-\infty}$ (ng · h/mL) | 3.32 | 1.39 | 239 | 215-264 | <0.001 |
| $t_{1/2}$ (h) | 1.18 | 1.19 | 102 | 94.0-111 | 0.6507 |

TABLE 5

Statistical Comparison of Geometric Least Squares Mean (GLSM) of Pharmacokinetic Parameters for IN Naloxone at a Dose of 4 mg to IM Naloxone at a Dose of 0.4 mg with No Dose Adjustment

| Parameter | GLSM 4 mg IN | GLSM 0.4 mg IM | GLSM Ratio IM/IN % | 90% CI of Ratio | p-value |
|---|---|---|---|---|---|
| $C_{max}$ (ng/mL) | 3.96 | 0.754 | 525 | 431-640 | <0.001 |
| $T_{max}$ (h) | 1.000 | 0.292 | 0.308 | 0.418 | | |
| $AUC_{0-t}$ (ng · h/mL) | 5.41 | 1.35 | 401 | 361-445 | <0.001 |
| $AUC_{0-\infty}$ (ng · h/mL) | 5.47 | 1.39 | 394 | 355-436 | <0.001 |
| $t_{1/2}$ (h) | 1.22 | 1.19 | 102 | 94.0-111 | 0.651 |

TABLE 6

Statistical Comparison of Geometric Least Squares Mean (GLSM) of Pharmacokinetic Parameters for IN Naloxone at a Dose of 2 mg to IM Naloxone at a Dose of 0.4 mg with Dose Adjustment to 0.4 mg

| Parameter | GLSM 2 mg IN | GLSM 0.4 mg IM | GLSM Ratio IM/IN % | 90% CI of Ratio | p-value |
|---|---|---|---|---|---|
| $C_{max/D}$ (ng/mL) | 0.510 | 0.755 | 67.6 | 55.3-82.7 | 0.0028 |
| $T_{max}$ (h) | 0.333 | 0.308 | — | — | 1.000 |
| $AUC_{0-t/D}$ (ng · h/mL) | 0.767 | 1.35 | 56.8 | 50.8-63.4 | <0.001 |
| $AUC_{0-\infty/D}$ (ng · h/mL) | 0.775 | 1.39 | 55.7 | 50.0-62.1 | <0.001 |
| $t_{1/2}$ (h) | 1.18 | 1.19 | 99.3 | 91.3-108 | 0.8963 |

TABLE 7

Statistical Comparison of Comparison of Geometric Least Squares Mean (GLSM) Pharmacokinetic Parameters for IN Naloxone at a Dose of 4 mg to IM Naloxone at a Dose of 0.4 mg with Dose Adjustment to 0.4 mg

| Parameter | GLSM 4 mg IN | GLSM 0.4 mg IM | GLSM Ratio IM/IN % | 90% CI of Ratio | p-value |
|---|---|---|---|---|---|
| $C_{max/D}$ (ng/mL) | 0.466 | 0.755 | 61.7 | 50.5-75.5 | <0.001 |
| $T_{max}$ (h) | 0.292 | 0.308 | — | — | 0.418 |
| $AUC_{0-t/D}$ (ng · h/mL) | 0.637 | 1.35 | 47.2 | 42.2-52.7 | <0.001 |
| $AUC_{0-\infty/D}$ (ng · h/mL) | 0.644 | 1.39 | 46.3 | 41.5-51.6 | <0.001 |
| $t_{1/2}$ (h) | 1.22 | 1.19 | 102 | 94.0-111 | 0.651 |

TABLE 8

Time to Prepare the IM and IN Doses for Administration

| | Time (seconds) | | |
|---|---|---|---|
| | IM Dose | 2 mg IN Dose | 4 mg IN Dose |
| N | 14 | 14 | 14 |
| Mean | 70 | 19 | 23 |
| SD | 10 | 4 | 3 |
| Median | 73 | 19 | 23 |
| Minimum | 50 | 15 | 18 |
| Maximum | 82 | 30 | 28 |

TABLE 9

Estimated IN Dose Delivered (mg)

| | | 4 mg Dose | | | |
|---|---|---|---|---|---|
| | 2 mg Dose Total | First Device | Second Device | Total | All Devices Total |
| N | 14 | 14 | 14 | 14 | 42 |
| Mean | 1.697 | 1.682 | 1.687 | 3.369 | 1.689 |
| SD | 0.097 | 0.156 | 0.092 | 0.193 | 0.116 |
| % CV | 5.7 | 9.3 | 5.4 | 5.7 | 6.9 |
| Median | 1.708 | 1.711 | 1.704 | 3.410 | 1.710 |
| Minimum | 1.481 | 1.315 | 1.506 | 2.898 | 1.315 |
| Maximum | 1.838 | 1.824 | 1.803 | 3.616 | 1.838 |

Example 2

Pharmacokinetics and Safety of Intranasal Naloxone in Humans (Study 2)

A second study was undertaken to determine the pharmacokinetics (PK) and bioavailability of intranasally-delivered naloxone compared to intramuscularly-injected naloxone.

Objectives.

Specifically, the study had several objectives. The first was to determine the pharmacokinetics (i.e., the $C_{max}$, $T_{max}$, $AUC_{0-inf}$ and $AUC_{0-t}$) of 4 intranasal doses—2 mg, 4 mg (2 nostrils), 4 mg (1 nostril), and 8 mg (2 nostrils)—of naloxone compared to a 0.4 mg dose of naloxone administrated IM and to identify an appropriate IN dose that could achieve systemic exposure comparable to an approved parenteral dose. The second was to determine the pharmacokinetics of two different concentrations (20 mg/mL and 40 mg/mL) of IN naloxone. The third was to determine the safety of IN naloxone, including adverse events, vital signs, and clinical laboratory changes, specifically with respect to nasal irritation (erythema, edema, and erosion).

Design.

The study was an inpatient open-label, randomized, 5-period, 5-treatment, 5-sequence, crossover study involving approximately 30 healthy volunteers, randomized to have at least 24 subjects who complete all study drug administrations and blood collections for PK assessments. Subjects were assigned to one of the 5 sequences and there were 6 subjects in each. Each subject received 5 naloxone treatments during the 5 dosing periods: a single 2 mg IN dose (one 0.1 mL spray of a 2.0 mg/mL solution in one nostril), a 4 mg IN dose (one 0.1 mL spray of a 20 mg/mL solution in each nostril), a single 4 mg IN dose (one 0.1 mL spray of a 40 mg/mL solution in one nostril), a single 8 mg IN dose (one 0.1 mL spray of a 40 mg/mL solution in each nostril), and a single 0.4 mg INT dose. Subjects stayed in an inpatient facility for 18 days to complete the entire study and were discharged on the next day after the last dose. Subjects returned for a final follow-up visit 3 to 5 days after discharge.

After obtaining informed consent, subjects were screened for eligibility to participate in the study including medical history, physical examination, clinical chemistry, coagulation markers, hematology, infectious disease serology, urinalysis, urine drug and alcohol toxicology screen, vital signs and ECG.

Inclusion criteria were: men or women 18 to 55 years of age, inclusive; written informed consent; BMI ranging from 18 to 30 kg/m2, inclusive; adequate venous access; no clinically significant concurrent medical conditions; agreement to use a reliable double-barrier method of birth control from the start of screening until one week after completing the study (oral contraceptives are prohibited); and agreement not to ingest alcohol, drinks containing xanthine >500 mg/day, or grapefruit/grapefruit juice, or participate in strenuous exercise 72 hours prior to admission through the last blood draw of the study.

Exclusion criteria were: any IN conditions including abnormal nasal anatomy, nasal symptoms (i.e., blocked and/or runny nose, nasal polyps, etc.), or having a product sprayed into the nasal cavity prior to drug administration; taking prescribed or over-the-counter medications, dietary supplements, herbal products, vitamins, or recent use of opioid analgesics for pain relief (within 14 days of last use of any of these products); positive urine drug test for alcohol, opioids, cocaine, amphetamine, methamphetamine, benzodiazepines, tetrahydrocannabinol (THC), barbiturates, or methadone at screening or admission; previous or current opioid, alcohol, or other drug dependence (excluding nicotine and caffeine), based on medical history; subject consumes greater than 20 cigarettes per day on average, in the month prior to screening, or would be unable to abstain from smoking (or use of any nicotine-containing substance) for at least one hour prior to and 2 hours after naloxone dosing; on standard 12-lead ECG, a QTcF interval >440 msec for males and >450 msec for females; significant acute or chronic medical disease in the judgment of the investigator; a likely need for concomitant treatment medication during the study; donated or received blood or underwent plasma or platelet apheresis within the 60 days prior to the day before study commencement; female who is pregnant, breast feeding, or plans to become pregnant during the study period or within one week after naloxone administration; positive test for hepatitis B surface antigen (HBsAg), hepatitis C virus antibody (HCVAb) or human immunodeficiency virus antibody (HIVAb) at screening; and current or recent (within 7 days prior to screening) upper respiratory tract infection.

Naloxone for IM injection manufactured by Hospira was obtained from a licensed distributor at a concentration of 0.4 mg/mL and was given IM at a dose of 0.4 mg in 1.0 mL with a 23-g needle as a single injection in the gluteus maximus muscle. Naloxone for IN administration was obtained from Lightlake Therapeutics, Inc., London, United Kingdom at two concentrations of 20 mg/mL and 40 mg/mL, and was given as doses of 2 mg (one 0.1 mL spray of the 20 mg/mL formulation in one nostril), 4 mg (two 0.1 mL sprays of the 20 mg/mL formulation in two nostrils), 4 mg (one 0.1 mL spray of the 40 mg/mL formulation in one nostril) and 8 mg (two 0.1 mL sprays of the 40 mg/mL formulation in two nostril). IN naloxone was administered using an Aptar single dose device with the subject in a fully supine position. Subjects were to be instructed to not breathe through the nose when the IN dose of naloxone was administered.

On the day after clinic admission, subjects were administered study drug in randomized order with a 4-day washout period between doses until all 5 treatments were administered. Blood was collected for naloxone PK prior to dosing and approximately 2.5, 5, 10, 15, 20, 30, 45, 60, 120, 180, 240, 300, 360, 480 and 720 minutes after the start of study drug administration, into sodium heparin containing tubes. On days of study drug administration, a 12-lead ECG was performed approximately 60 minutes prior to dosing and at approximately 60 and 480 minutes post-dose. Vital signs were measured pre-dose and approximately 30, 60, 120, and 480 minutes post-dose. On dosing days, the order of assessments were ECG, vital signs, then PK blood collection when scheduled at the same nominal times. The target time of the PK blood collection was considered the most important, and if the collection was more than ±1 minute from the scheduled time for the first 60 minutes of collections or more than ±5 minutes for the scheduled time points thereafter, this was considered a protocol deviation. ECG and vital signs were collected within the 10 minute period before the nominal time of blood collections. At screening, admission, discharge, and follow-up, ECG and vital signs were checked once per day. Vital signs were also checked once on the day after naloxone administration. Clinical laboratory measurements were repeated after the last PK blood draw prior to clinic discharge. Adverse events were assessed by spontaneous reports by subjects, by examination of the nasal mucosa, by measuring vital signs, ECG, and clinical laboratory parameters.

Figure 3:
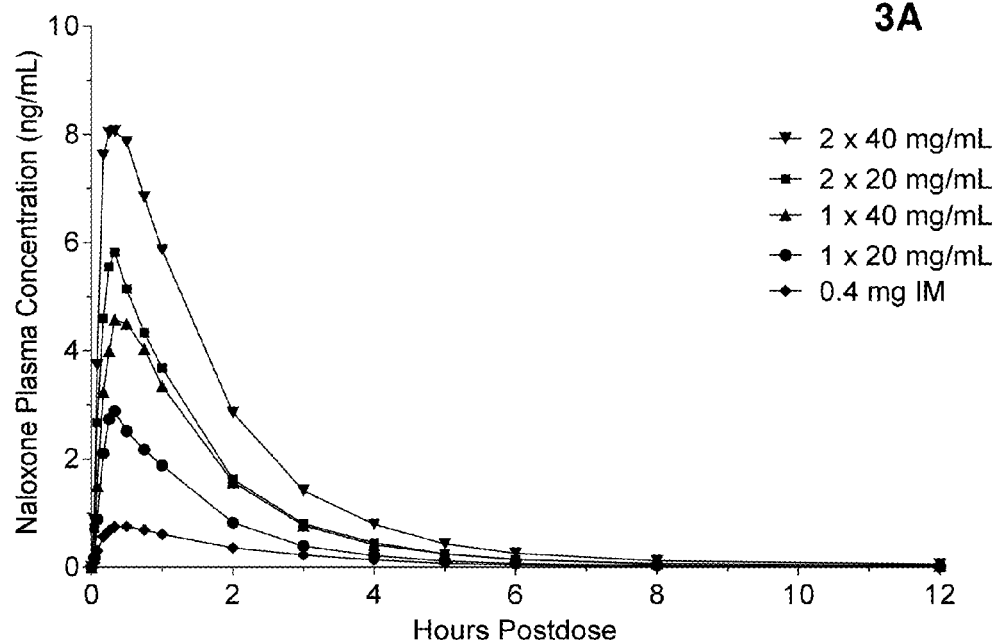
FIG. 3 shows the mean naloxone plasma concentration following single intranasal administrations (FIG. 3A) and intramuscular injections (FIG. 3B) of naloxone to healthy subjects (N=28) over a twelve-hour period.
Figure 3:
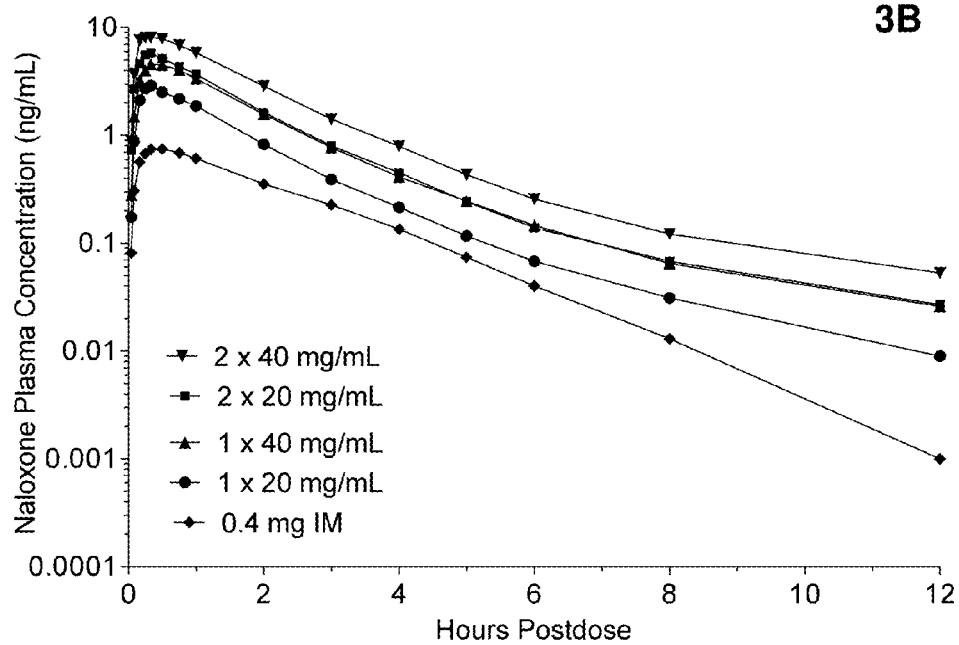
Figure 4:
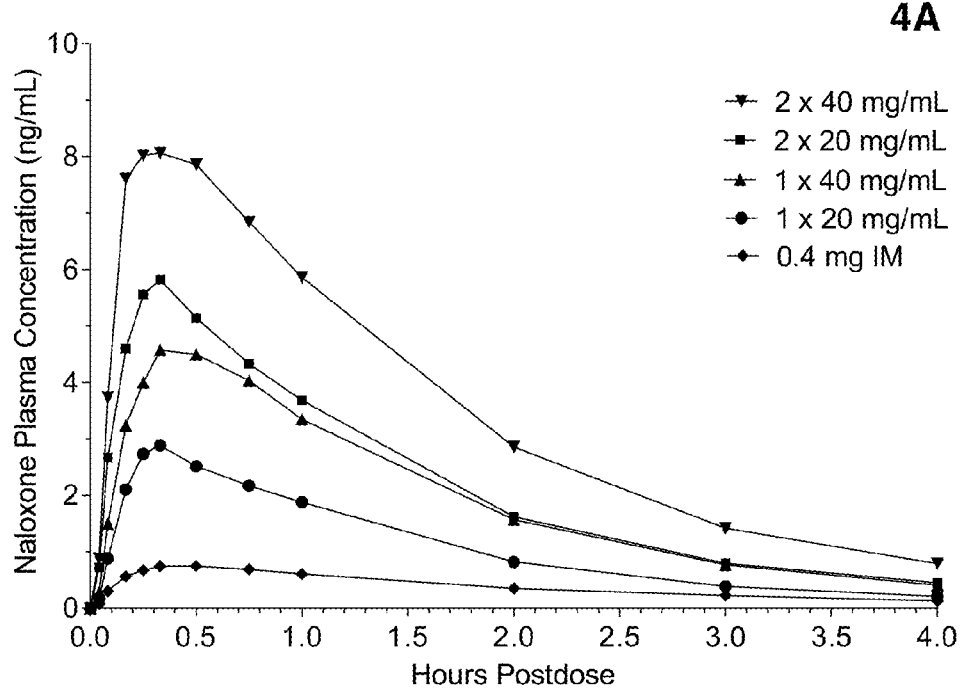
FIG. 4 shows the mean naloxone plasma concentration following single intranasal administrations (FIG. 4A) and intramuscular injections (FIG. 4B) of naloxone to healthy subjects (N=28) over a four-hour period.
Figure 4:
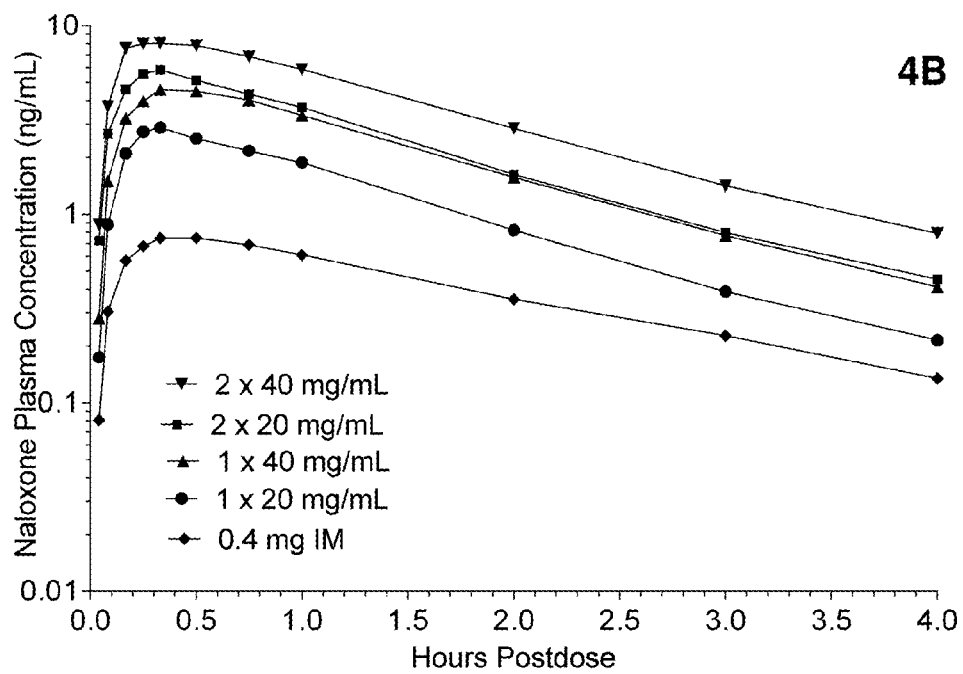
Figure 5:
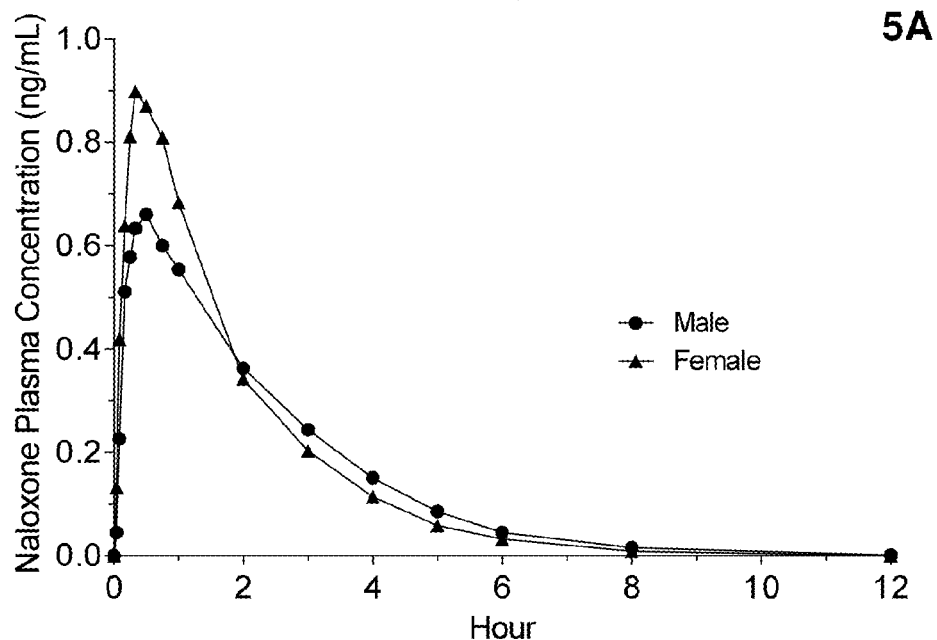
FIG. 5 shows the mean naloxone plasma concentration following intramuscular injection of 0.4 mg naloxone (FIG. 5A, top) and one spray of 20 mg/mL naloxone (FIG. 5B, bottom) to healthy male (N=16) and female (N=12) subjects over a twelve-hour period.
Figure 5:
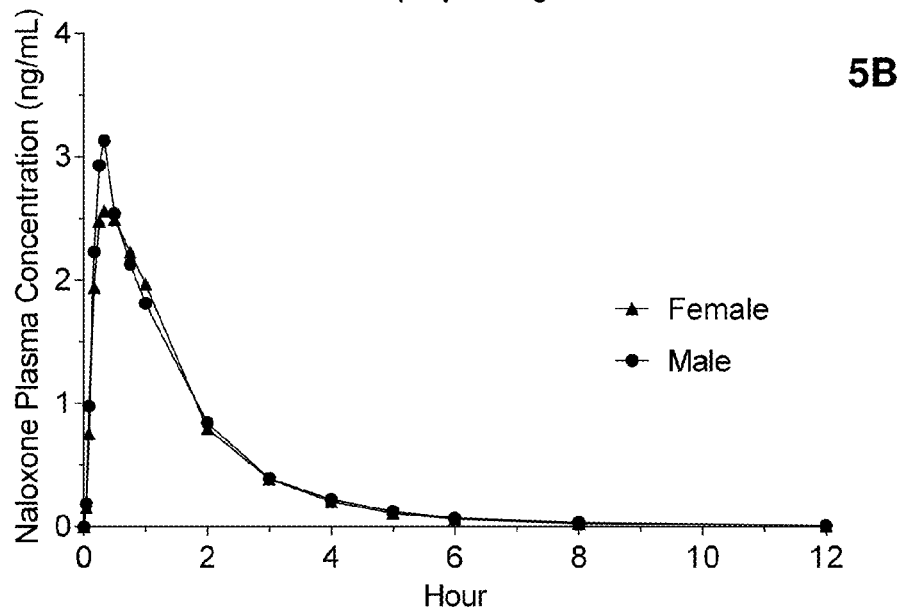
Figure 6:
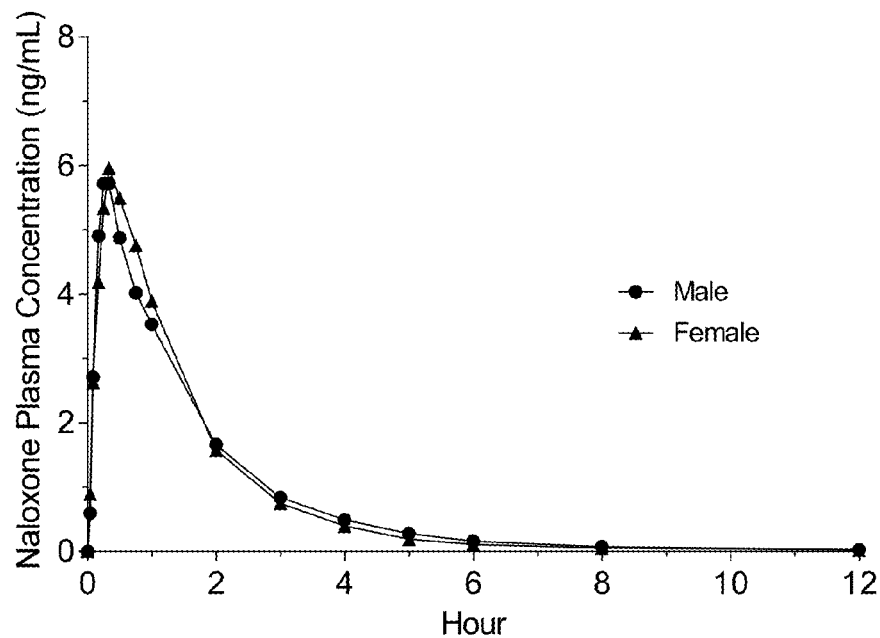
FIG. 6 shows the mean naloxone plasma concentration following two sprays of 20 mg/mL (FIG. 6A, top) and one spray of 40 mg/mL (FIG. 6B, bottom) to healthy male (N=16) and female (N=12) subjects over a twelve-hour period.
Figure 6:
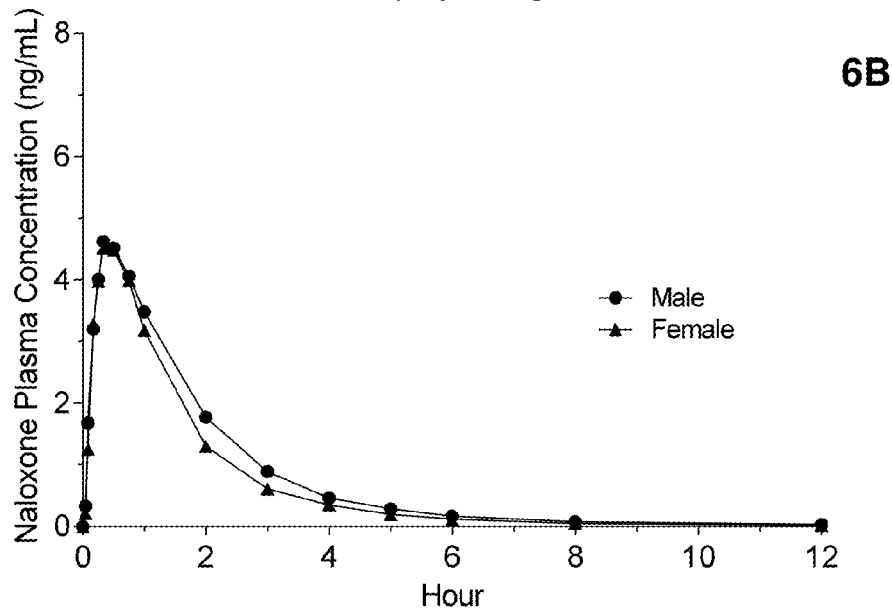
Figure 7:
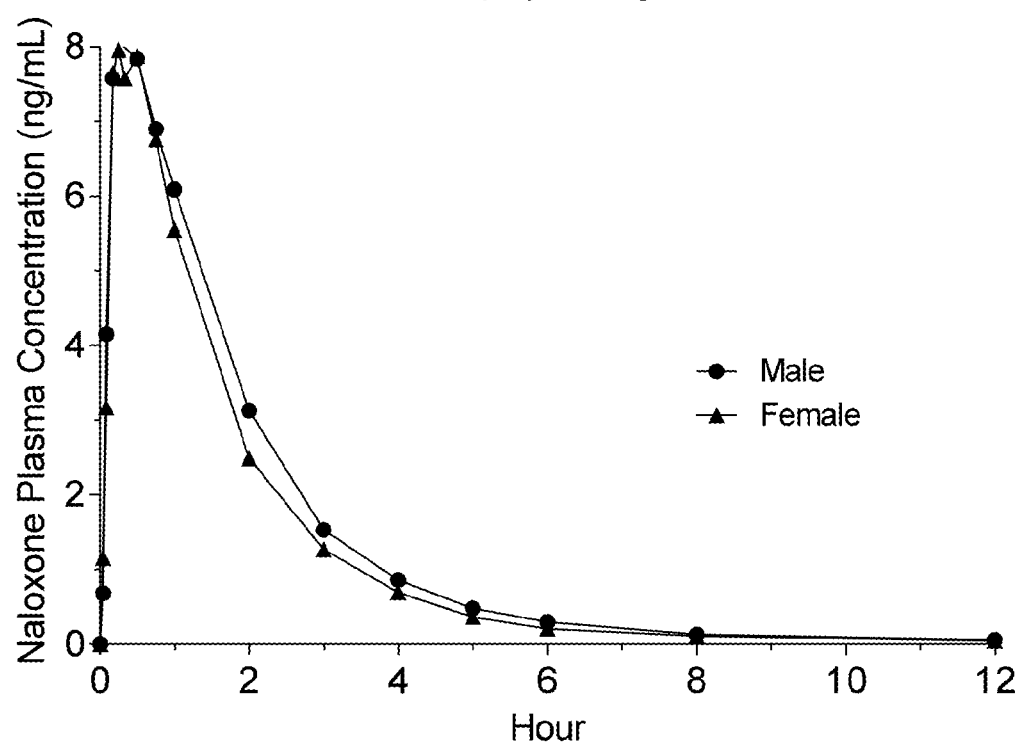
FIG. 7 shows the mean naloxone plasma concentration following two sprays of 40 mg/mL to healthy male (N=16) and female (N=12) subjects over a twelve-hour period.

Results are shown below in Table 9, which sets forth the mean from 28 healthy subjects (and SD, in parentheses) plasma concentrations of naloxone following single intranasal administrations and an intramuscular injection, and in FIGS. 3 and 4.

TABLE 9

| Time (min) | One Spray - 2 mg 20 mg/mL IN | | Two Sprays - 4 mg 20 mg/mL IN | | One Spray - 4 mg 40 mg/mL IN | | Two Sprays - 8 mg 40 mg/mL IN | | 0.4 mg IM | |
|---|---|---|---|---|---|---|---|---|---|---|
| 0 | 0.000 | (0.000) | 0.000 | (0.000) | 0.000 | (0.000) | 0.000 | (0.000) | 0.000 | (0.000) |
| 2.5 | 0.175 | (0.219) | 0.725 | (0.856) | 0.280 | (0.423) | 0.880 | (1.21) | 0.081 | (0.135) |
| 5 | 0.882 | (0.758) | 2.68 | (2.65) | 1.50 | (1.76) | 3.73 | (4.02) | 0.305 | (0.336) |
| 10 | 2.11 | (1.33) | 4.60 | (2.59) | 3.24 | (2.21) | 7.61 | (5.28) | 0.566 | (0.318) |
| 15 | 2.74 | (1.07) | 5.56 | (2.20) | 4.00 | (2.24) | 8.02 | (3.60) | 0.678 | (0.312) |
| 20 | 2.89 | (1.14) | 5.82 | (1.74) | 4.57 | (2.30) | 8.06 | (2.56) | 0.747 | (0.271) |
| 30 | 2.52 | (0.810) | 5.15 | (1.70) | 4.50 | (1.93) | 7.89 | (1.95) | 0.750 | (0.190) |
| 45 | 2.17 | (0.636) | 4.33 | (1.16) | 4.03 | (1.57) | 6.84 | (1.69) | 0.689 | (0.171) |
| 60 | 1.88 | (0.574) | 3.69 | (0.887) | 3.35 | (1.17) | 5.86 | (1.40) | 0.610 | (0.143) |
| 120 | 0.823 | (0.335) | 1.63 | (0.626) | 1.57 | (0.773) | 2.86 | (0.927) | 0.354 | (0.107) |
| 180 | 0.390 | (0.146) | 0.800 | (0.253) | 0.771 | (0.412) | 1.42 | (0.487) | 0.227 | (0.082) |
| 240 | 0.215 | (0.100) | 0.452 | (0.225) | 0.412 | (0.215) | 0.791 | (0.275) | 0.135 | (0.058) |
| 300 | 0.117 | (0.051) | 0.243 | (0.123) | 0.246 | (0.143) | 0.431 | (0.166) | 0.074 | (0.047) |
| 360 | 0.068 | (0.030) | 0.139 | (0.067) | 0.146 | (0.081) | 0.257 | (0.104) | 0.040 | (0.022) |
| 480 | 0.031 | (0.014) | 0.068 | (0.033) | 0.065 | (0.038) | 0.122 | (0.052) | 0.013 | (0.015) |
| 720 | 0.009 | (0.009) | 0.027 | (0.013) | 0.026 | (0.019) | 0.053 | (0.025) | 0.001 | (0.003) |

For pharmacokinetic analysis, plasma was separated from whole blood and stored frozen at ≤−20° C. until assayed. Naloxone plasma concentrations was determined by liquid chromatography with tandem mass spectrometry. Conjugated naloxone plasma concentrations may also be determined. Non-compartmental PK parameters including $C_{max}$, $T_{max}$, $AUC_{0-inf}$, $AUC_{0-t}$, $t_{1/2}$, $\lambda_z$, and apparent clearance (CL/F) were determined. Pharmacokinetic parameters ($C_{max}$, $T_{max}$, and AUCs) for IN naloxone were compared with those for IM naloxone. $T_{max}$ was from the time of administration (spraying into the nasal cavity or IM injection). Dose adjusted values for AUCs and $C_{max}$ were then calculated, and the relative extent of intranasal absorption (IN versus IM) estimated from the dose-corrected AUCs. Within an ANOVA framework, comparisons of ln-transformed PK parameters ($C_{max}$ and AUC) for intranasal versus IM naloxone treatments were performed. The 90% confidence interval for the ratio (IN/IM) of the geometric least squares means of AUC and $C_{max}$ parameters were constructed for comparison of each treatment with IM naloxone. These 90% CIs were obtained by exponentiation of the 90% confidence intervals for the difference between the least squares means based upon an ln scale.

Results are shown below in Table 10, which sets forth the mean plasma PK parameters from 28 healthy subjects (and % CV, in parentheses) of naloxone following single intranasal administrations and an intramuscular injection, and in Table 11, which sets forth the same PK parameters split between the 12 female and 16 male healthy subjects.

TABLE 10

| Parameter (units) | One Spray - 2 mg 20 mg/mL IN | Two Sprays - 4 mg 20 mg/mL IN | One Spray - 4 mg 40 mg/mL IN | Two Sprays - 8 mg 40 mg/mL IN | 0.4 mg IM |
|---|---|---|---|---|---|
| $C_{max}$ (ng/ml) | 3.11 (36.3) | 6.63 (34.2) | 5.34 (44.1) | 10.3 (38.8) | 0.906 (31.5) |
| $C_{max}$ per mg (ng/mL) | 1.56 (36.3) | 1.66 (34.2) | 1.34 (44.1) | 1.29 (38.8) | 2.26 (31.5) |
| $T_{max}$ (h)[a] (median, range) | 0.33 (0.25, 1.00) | 0.33 (0.08, 0.50) | 0.50 (0.17, 1.00) | 0.33 (0.17, 1.00) | 0.42 (0.08, 2.00) |
| $AUC_t$ (ng · mL/h) | 4.81 (30.3) | 9.82 (27.3) | 8.78 (37.4) | 15.9 (23.6) | 1.79 (23.5) |
| $AUC_{inf}$ (ng · mL/h) | 4.86 (30.1) | 9.91 (27.1) | 8.87 (37.2) | 16.1 (23.3) | 1.83 (23.0) |
| $AUC_{inf}$ per mg (ng · mL/h) | 2.43 (30.1) | 2.48 (27.1) | 2.22 (37.2) | 2.01 (23.3) | 4.57 (23.0) |
| Lambda z ($hr^{-1}$)[b] | 0.3685 | 0.2973 | 0.3182 | 0.3217 | 0.5534 |
| Half-life (h)[b] | 1.70 | 2.09 | 2.00 | 1.91 | 1.19 |
| AUC % Extrapolate | 1.09 (41.9) | 1.01 (53.9) | 1.06 (52.5) | 1.04 (78.1) | 2.32 (54.1) |
| CL/F (L/h) | 441 (24.5) | 426 (22.3) | 502 (31.2) | 521 (21.7) | 230 (22.4) |
| Relative BA (%) vs. IM | 53.8 (22.2) | 55.3 (22.2) | 49.2 (30.6) | 45.3 (25.1) | 100 |

TABLE 11

| Parameter (units) | One 20 mg/mL IN | | Two 20 mg/mL IN | | One 40 mg/mL IN | | Two 40 mg/mL IN | | 0.4 mg IM | |
|---|---|---|---|---|---|---|---|---|---|---|
| | Female | Male | Female | Male | Female | Male | Female | Male | Female | Male |
| $C_{max}$ (ng/ml) | 2.79 | 3.35 | 6.62 | 6.64 | 5.12 | 5.51 | 9.52 | 10.9 | 1.06 | 0.792 |

TABLE 11-continued

| Parameter (units) | One 20 mg/mL IN | | Two 20 mg/mL IN | | One 40 mg/mL IN | | Two 40 mg/mL IN | | 0.4 mg IM | |
|---|---|---|---|---|---|---|---|---|---|---|
| | Female | Male | Female | Male | Female | Male | Female | Male | Female | Male |
| $C_{max}$ per mg (ng/mL) | 1.39 | 1.68 | 1.66 | 1.66 | 1.28 | 1.38 | 1.19 | 1.36 | 2.64 | 1.98 |
| $T_{max}$ (h)$^a$ | 0.33 | 0.33 | 0.33 | 0.25 | 0.50 | 0.50 | 0.29 | 0.42 | 0.33 | 0.50 |
| $AUC_t$ (ng · mL/h) | 4.73 | 4.87 | 9.81 | 9.82 | 7.98 | 9.38 | 14.8 | 16.8 | 1.83 | 1.75 |
| $AUC_{inf}$ (ng · mL/h) | 4.78 | 4.93 | 9.91 | 9.92 | 8.06 | 9.48 | 15.0 | 16.9 | 1.88 | 1.79 |
| $AUC_{inf}$ per mg (ng · mL/h) | 2.39 | 2.46 | 2.48 | 2.48 | 2.01 | 2.37 | 1.87 | 2.12 | 4.69 | 4.47 |
| Lambda z $(hr^{-1})^b$ | 0.3978 | 0.3492 | 0.2796 | 0.3122 | 0.2946 | 0.3386 | 0.2994 | 0.3407 | 0.6140 | 0.5152 |
| Half-life (h)$^b$ | 1.58 | 1.80 | 2.18 | 2.03 | 2.12 | 1.93 | 1.90 | 1.91 | 1.08 | 1.28 |
| AUC % Extrapolate | 0.971 | 1.19 | 0.986 | 1.02 | 0.970 | 1.12 | 1.12 | 0.992 | 2.31 | 2.32 |
| CL/F (L/h) | 449 | 434 | 419 | 431 | 555 | 462 | 558 | 494 | 222 | 236 |

In the tables above, the notation a indicates median (range) is disclosed, and the notation b indicates harmonic mean is disclosed.

Additional exploratory analyses could include:

1) 90% CI for dose corrected AUC and $C_{max}$ between the 20 mg/mL formulation treatment and 40 mg/mL formulation for both a single administration and two dose administration (once in each nostril) for dose linearity purpose;

2) 90% CI adjusted for dose for geometric ratios of one 0.1 mL spray (in one nostril) vs. a two 0.1 mL sprays (one spray in each nostril) from an 20 mg/mL formulation; and 3) 90% CI adjusted for dose for geometric ratios of one 0.1 mL spray (in one nostril) vs. a two 0.1 mL sprays (one spray in each nostril) from an 40 mg/mL formulation;

AEs were coded using the most recent version of the Medical Dictionary for Regulatory Activities (MedDRA) preferred terms and grouped by system, organ, class (SOC) designation. Separate summaries will be provided for the 5 study periods: after the administration of each dose of study drug up until the time of the next dose of study drug or clinic discharge. Listings of each individual AE including start date, stop date, severity, relationship, outcome, and duration were provided. Results are given below in Tables 12 and 13. Table 12 shows the events related to nasal irritation—erythema, edema, other, and total—observed in the nasally-treated group. Nasal irritation did not appear to be positively related to the dose of naloxone given.

TABLE 12

| Treatment | Erythema | Edema | Other | Total |
|---|---|---|---|---|
| 2 mg (20 mg/mL, one spray) | 4 | 2 | 1 | 7 |
| 4 mg (20 mg/mL, two sprays) | 1 | 0 | 0 | 1 |
| 4 mg (40 mg/mL, one spray) | 1 | 2 | 0 | 3 |
| 8 mg (40 mg/mL, two sprays) | 0 | 1 | 0 | 1 |

Table 1e shows additional events related to administration either nasally or intramuscularly. Overall, few adverse events were reported.

TABLE 13

| 0.4 mg Intramuscular Dose | |
|---|---|
| Dizziness | 1 |
| Headache | 1 |
| Nausea | 1 |
| 2 mg (20 mg/mL, one spray) | |
| Nasal Pain | 1 |
| 8 mg (40 mg/mL, two sprays) | |
| Headache | 1 |

Additionally, vital signs, ECG, and clinical laboratory parameters did not reveal any clinically noteworthy changes after naloxone administration. There was no evidence of QTcF prolongation.

Example 3

Naloxone Nasal Spray Formulations and Stability

Naloxone has been formulated as a disposable Luer-Jet Luer-lock pre-filled syringe and nasal atomizer kit product, comprising 1 mg/ml naloxone hydrochloride as an active agent, 8.35 mg/ml NaCl as an isotonicity agent, HCl q.s. to target pH, and purified water q.s. to 2.0 ml. Benzalkonium chloride may be added as a preservative, cationic surfactant, and/or permeation enhancer, and supports the stability of a multi-dose product. Such syringes, while functional, can be ungainly to use by untrained personnel, and deliver a large volume of solution.

Examples of a 10 mg/ml formulation are given below in Table 14.

TABLE 14

| Ingredient | Quantity per unit | Function |
|---|---|---|
| Naloxone hydrochloride | 10 mg/ml | Active ingredient |
| Sodium chloride | 7.4 mg/ml | Isotonicity agent |
| Hydrochloric acid | q.s. to target pH | Acidifying agent |
| Benzalkonium chloride | 0.1 mg/ml | Preservative, cationic surfactant, and/or permeation enhancer |
| Purified water | q. s. | Solvent |

Literature data has indicated that naloxone is sensitive to environmental factors, such as air, light and colours in certain vials, which may induce a risk for degradation. Consequently disodium edetate was added to the above formulation.

Pharmaceutical compositions comprising naloxone hydrochloride (10 mg/mL) were stored at 25° C. and 60% relative humidity in upright clear glass vials (200 μL) stoppered with a black plunger. Vials were either nude (Batch 1), or mounted in the Pfeiffer BiDose device (Batch 2). In addition to naloxone hydrochloride, the pharmaceutical compositions further comprised water, benzalkonium chloride, and disodium edetate. The vials were assayed at 0, 3, 6, 9, and 12 months for naloxone content. It is evident from the results of the study, reported as a percentage of the label claim in Table 15 below, that these pharmaceutical compositions are storage-stable for at least 9-12 months at 25° C. and 60% relative humidity.

TABLE 15

| Batch | Time (months) | | | | |
|---|---|---|---|---|---|
| | 0 | 3 | 6 | 9 | 12 |
| 1 | 99.3 | 100.1 | 100.8 | 101.2 | 97.9 |
| 2 | 99.5 | 102.8 | 99.4 | 98.6 | ND |

Examples of 20 mg/ml and a 40 mg/ml formulation are given below in Table 16, along with an example of permitted variation as part of the total formulation.

TABLE 16

| | 20 mg/ml | | 40 mg/ml | | |
|---|---|---|---|---|---|
| Concentration Component | Quantity per ml | Quantity per unit dose (100 μl) | Quantity per ml | Quantity per unit dose (100 μl) | Product Variation |
| Naloxone HCl dihydrate (corresponding to naloxone HCl) | 22.0 mg (20.0 mg) | 2.2 mg (2.0 mg) | 44.0 mg (40.0 mg) | 4.4 mg (40.0 mg) | 90.0-110.0 |
| Benzalkonium chloride | 0.1 mg | 0.01 mg | 0.1 mg | 0.01 mg | 90.0-110.0 |
| Disodium edetate | 2.0 mg | 0.2 mg | 2.0 mg | 0.2 mg | 80.0-120.0 |
| Sodium chloride | 7.4 mg | 0.74 mg | 7.4 mg | 0.74 mg | |
| Hydrochloric acid, dilute | Adjust to pH 4.5 | Adjust to pH 4.5 | Adjust to pH 4.5 | Adjust to pH 4.5 | pH 3.5-5.5 |
| Purified water | q.s. ad 1.0 ml | q.s. ad 100 μl | q.s. ad 1.0 ml | q.s. ad 100 μl | |

The naloxone hydrochloride nasal spray above is an aqueous solution which may be presented in a Type I glass vial closed with a chlorobutyl rubber plunger which in turn is mounted into a unit-dose nasal spray device (such as an Aptar UDS liquid UnitDose device). The solution should be a clear and colorless or slightly yellow liquid. In certain embodiments, the device is a non-pressurized dispenser delivering a spray containing a metered dose of the active ingredient. In certain embodiments, each delivered dose contains 100 μl.

Pharmaceutical compositions comprising naloxone hydrochloride (20 or 40 mg/mL) were tested for stability in room temperature/light conditions, room temperature/dark conditions and in 25° C./60% RH (protected from light). It was tested for pH, purity, and impurities at an initial time point, 2 months and 10 months. Results are given in Table 17.

TABLE 17

| Storage condition | Test interval (months) | Appearance | pH | Assay (% of label claim) | Impurities (area %) |
|---|---|---|---|---|---|
| | Initial | Clear, colourless solution | 4.5 | 101 | Not detected |
| 25° C./60% RH | 2 | Not analyzed | 45 | Not analyzed | Not analyzed |
| | 10 | Clear, colourless solution | 4.5 | 95 | 0.2 |
| Room temperature/ light | 10 | Clear, yellow solution | 4.4 | 92 | 1.3 |
| Room temperature/ dark | 10 | Clear, colourless solution | 4.5 | 97 | 0.3 |

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A single-use, pre-primed device adapted for nasal delivery of a pharmaceutical composition to a patient by one actuation of said device into one nostril of said patient, having a single reservoir comprising a pharmaceutical composition which is an aqueous solution of about 100 μL comprising:
   about 2 mg naloxone hydrochloride or a hydrate thereof;
   between about 0.2 mg and about 1.2 mg of an isotonicity agent;
   between about 0.005 mg and about 0.015 mg of a compound which is at least one of a preservative, a cationic surfactant, and a permeation enhancer;

between about 0.1 mg and about 0.5 mg of a stabilizing agent; and an amount of an acid sufficient to achieve a pH of 3.5-5.5.

2. The device of claim 1 wherein:
the isotonicity agent is NaCl;
the compound which is at least one of a preservative, a cationic surfactant, and a permeation enhancer is benzalkonium chloride;
the stabilizing agent is disodium edetate; and
the acid is hydrochloric acid.

3. The device of claim 2, wherein the aqueous solution comprises:
about 2.2 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH of 3.5-5.5.

4. The device of claim 2, wherein said device is actuatable with one hand.

5. The device of claim 4, wherein the volume of said reservoir is not more than about 140 μL.

6. The device of claim 5, wherein about 100 μL of said aqueous solution in said reservoir is delivered to said patient in one actuation.

7. The device of claim 6, wherein the pharmaceutical composition which is an aqueous solution comprises about 2.2 mg naloxone hydrochloride dihydrate.

8. The device of claim 7, wherein the 90% confidence interval for dose delivered per actuation is ±about 2%.

9. The device of claim 7, wherein the 95% confidence interval for dose delivered per actuation is ±about 2.5%.

10. The device of claim 7, wherein the delivery time is less than about 25 seconds.

11. The device of claim 7, wherein the delivery time is less than about 20 seconds.

12. The device of claim 7, wherein the device is configured such that upon nasal delivery of said pharmaceutical composition to said patient, less than about 20% of said pharmaceutical composition leaves the nasal cavity via drainage into the nasopharynx or externally.

13. The device of claim 12, wherein the device is configured such that upon nasal delivery of said pharmaceutical composition to said patient, less than about 10% of said pharmaceutical composition leaves the nasal cavity via drainage into the nasopharynx or externally.

14. The device of claim 13, wherein the device is configured such that upon nasal delivery of said pharmaceutical composition to said patient, less than about 5% of said pharmaceutical composition leaves the nasal cavity via drainage into the nasopharynx or externally.

15. The device of claim 7, wherein the plasma concentration versus time curve of said naloxone hydrochloride in said patient has a $T_{max}$ of between about 20 and about 30 minutes.

16. A pharmaceutical formulation for intranasal administration comprising, in an aqueous solution of not more than about 140 μL
about 2 mg naloxone hydrochloride or a hydrate thereof;
between about 0.2 mg and about 1.2 mg of an isotonicity agent;
between about 0.005 mg and about 0.015 mg of a compound which is at least one of a preservative, a cationic surfactant, and a permeation enhancer;
between about 0.1 mg and about 0.5 mg of a stabilizing agent;
an amount of an acid sufficient to achieve a pH of 3.5-5.5.

17. The pharmaceutical formulation of claim 16, wherein the naloxone hydrochloride is provided as naloxone hydrochloride dihydrate.

18. The pharmaceutical formulation of claim 17 wherein:
the isotonicity agent is NaCl;
the compound which is at least one of a preservative, a cationic surfactant, and a permeation enhancer is benzalkonium chloride;
the stabilizing agent is disodium edetate; and
the acid is hydrochloric acid.

19. The pharmaceutical formulation of claim 18, wherein the aqueous solution comprises:
about 2.2 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH of 3.5-5.5.

20. A method of treatment of opioid overdose or a symptom thereof, comprising nasally administering to a patient in need thereof a dose of naloxone hydrochloride using a single-use, pre-primed device adapted for nasal delivery of a pharmaceutical composition to a patient by one actuation of said device into one nostril of said patient, having a single reservoir comprising a pharmaceutical composition which is an aqueous solution of about 100 μL comprising:
about 2 mg naloxone hydrochloride or a hydrate thereof;
between about 0.2 mg and about 1.2 mg of an isotonicity agent;
between about 0.005 mg and about 0.015 mg of a compound which is at least one of a preservative, a cationic surfactant, and a permeation enhancer;
between about 0.1 mg and about 0.5 mg of a stabilizing agent; and
an amount of an acid sufficient to achieve a pH of 3.5-5.5.

21. The method of claim 20, wherein the naloxone hydrochloride is provided as naloxone hydrochloride dihydrate.

22. The method of claim 21 wherein:
the isotonicity agent is NaCl;
the compound which is at least one of a preservative, a cationic surfactant, and a permeation enhancer is benzalkonium chloride;
the stabilizing agent is disodium edetate; and
the acid is hydrochloric acid.

23. The method of claim 22, wherein the aqueous solution comprises:
about 2.2 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH of 3.5-5.5.

24. The method of claim 20, wherein said device is actuatable with one hand.

25. The method of claim 24, wherein the volume of said reservoir is not more than about 140 μL.

26. The method of claim 25, wherein about 100 μL of said aqueous solution in said reservoir is delivered to said patient in one actuation.

27. The method of claim 26, wherein the pharmaceutical composition which is an aqueous solution comprises about 2.2 mg naloxone hydrochloride dihydrate.

28. The method of claim 27, wherein the 90% confidence interval for dose delivered per actuation is ± about 2%.

29. The method of claim 27, wherein the 95% confidence interval for dose delivered per actuation is ± about 2.5%.

30. The method of claim 27, wherein the delivery time is less than about 25 seconds.

31. The method of claim 27, wherein the delivery time is less than about 20 seconds.

32. The method of claim 23, wherein upon nasal delivery of said pharmaceutical composition to said patient, less than about 20% of said pharmaceutical composition leaves the nasal cavity via drainage into the nasopharynx or externally.

33. The method of claim 23, wherein upon nasal delivery of said pharmaceutical composition to said patient, less than about 10% of said pharmaceutical composition leaves the nasal cavity via drainage into the nasopharynx or externally.

34. The method of claim 23, wherein upon nasal delivery of said pharmaceutical composition to said patient, less than about 5% of said pharmaceutical composition leaves the nasal cavity via drainage into the nasopharynx or externally.

35. The method of claim 20, wherein the plasma concentration versus time curve of said naloxone hydrochloride in said patient has a $T_{max}$ of between about 20 and about 30 minutes.

36. The method of claim 20, wherein said patient is an opioid overdose patient or a suspected opioid overdose patient.

37. The method of claim 36, wherein the patient exhibits one or more symptoms chosen from: respiratory depression, central nervous system depression, cardiovascular depression, altered level consciousness, miotic pupils, hypoxemia, acute lung injury, aspiration pneumonia, sedation, hypotension, unresponsiveness to stimulus, unconsciousness, stopped breathing; erratic or stopped pulse, choking or gurgling sounds, blue or purple fingernails or lips, slack or limp muscle tone, contracted pupils, and vomiting.

38. The method of claim 37, wherein the patient exhibits respiratory depression.

39. The method of claim 38, wherein said respiratory depression is caused by the illicit use of opioids, or by an accidental misuse of opioids during medical opioid therapy.

40. The method of claim 38, wherein said patient is free from respiratory depression for at least about 1 hour following treatment comprising delivery of said therapeutically effective amount of said opioid antagonist.

41. The method of claim 40, wherein said patient is free from respiratory depression for at least about 2 hours following treatment comprising delivery of said therapeutically effective amount of said opioid antagonist.

42. The method of claim 40, wherein said patient is free from respiratory depression for at least about 4 hours following treatment comprising delivery of said therapeutically effective amount of said opioid antagonist.

43. The method of claim 40, wherein said patient is free from respiratory depression for at least about 6 hours following treatment comprising delivery of said therapeutically effective amount of said opioid antagonist.

44. The method of claim 40, wherein said patient is in a lying, supine, or recovery position.

45. A method of complete or partial reversal of narcotic depression or respiratory depression induced by opioids in a patient, comprising nasally administering to a patient in need thereof a dose of naloxone hydrochloride using a single-use, pre-primed device adapted for nasal delivery of a pharmaceutical composition to a patient by one actuation of said device into one nostril of said patient, having a single reservoir comprising a pharmaceutical composition which is an aqueous solution of about 100 µL comprising:
about 2 mg naloxone hydrochloride or a hydrate thereof;
between about 0.2 mg and about 1.2 mg of an isotonicity agent;
between about 0.005 mg and about 0.015 mg of a compound which is at least one of a preservative, a cationic surfactant, and a permeation enhancer;
between about 0.1 mg and about 0.5 mg of a stabilizing agent; and
an amount of an acid sufficient to achieve a pH of 3.5-5.5.

46. The method of claim 45, wherein the naloxone hydrochloride is provided as naloxone hydrochloride dihydrate.

47. The method of claim 46, wherein:
the isotonicity agent is NaCl;
the compound which is at least one of a preservative, a cationic surfactant, and a permeation enhancer is benzalkonium chloride;
the stabilizing agent is disodium edetate; and
the acid is hydrochloric acid.

48. The method of claim 45, wherein the aqueous solution comprises:
about 2.2 mg naloxone hydrochloride dihydrate;
about 0.74 mg NaCl;
about 0.01 mg benzalkonium chloride;
about 0.2 mg disodium edetate; and
an amount of hydrochloric acid sufficient to achieve a pH of 3.5-5.5.

49. The method of claim 45, wherein said method is actuatable with one hand.

50. The method of claim 49, wherein the volume of said reservoir is not more than about 140 µL.

51. The method of claim 50, wherein about 100 µL of said aqueous solution in said reservoir is delivered to said patient in one actuation.

52. The method of claim 51, wherein the pharmaceutical composition which is an aqueous solution comprises about 2.2 mg naloxone hydrochloride dihydrate.

53. The method of claim 52, wherein the 90% confidence interval for dose delivered per actuation is ± about 2%.

54. The method of claim 52, wherein the 95% confidence interval for dose delivered per actuation is ± about 2.5%.

55. The method of claim 52, wherein the delivery time is less than about 25 seconds.

56. The method of claim 52, wherein the delivery time is less than about 20 seconds.

57. The method of claim 48, wherein upon nasal delivery of said pharmaceutical composition to said patient, less than about 20% of said pharmaceutical composition leaves the nasal cavity via drainage into the nasopharynx or externally.

58. The method of claim 48, wherein upon nasal delivery of said pharmaceutical composition to said patient, less than about 10% of said pharmaceutical composition leaves the nasal cavity via drainage into the nasopharynx or externally.

59. The method of claim 48, wherein upon nasal delivery of said pharmaceutical composition to said patient, less than about 5% of said pharmaceutical composition leaves the nasal cavity via drainage into the nasopharynx or externally.

60. The method of claim 45, wherein the plasma concentration versus time curve of said naloxone hydrochloride in said patient has a $T_{max}$ of between about 20 and about 30 minutes.

61. The method of claim 45, wherein said patient is an opioid overdose patient or a suspected opioid overdose patient.

62. The method of claim 61, wherein the patient exhibits one or more symptoms chosen from: respiratory depression, central nervous system depression, cardiovascular depression, altered level consciousness, miotic pupils, hypoxemia, acute lung injury, aspiration pneumonia, sedation, hypotension, unresponsiveness to stimulus, unconsciousness, stopped breathing; erratic or stopped pulse, choking or gurgling sounds, blue or purple fingernails or lips, slack or limp muscle tone, contracted pupils, and vomiting.

63. The method of claim 62, wherein the patient exhibits respiratory depression.

64. The method of claim 63, wherein said respiratory depression is caused by the illicit use of opioids, or by an accidental misuse of opioids during medical opioid therapy.

65. The method of claim 63, wherein said patient is free from respiratory depression for at least about 1 hour following treatment comprising delivery of said therapeutically effective amount of said opioid antagonist.

66. The method of claim 65, wherein said patient is free from respiratory depression for at least about 2 hours following treatment comprising delivery of said therapeutically effective amount of said opioid antagonist.

67. The method of claim 66, wherein said patient is free from respiratory depression for at least about 4 hours following treatment comprising delivery of said therapeutically effective amount of said opioid antagonist.

68. The method of claim 67, wherein said patient is free from respiratory depression for at least about 6 hours following treatment comprising delivery of said therapeutically effective amount of said opioid antagonist.

69. The method of claim 61, wherein said patient is in a lying, supine, or recovery position.

* * * * *